United States Patent
Jung et al.

(10) Patent No.: US 10,184,181 B2
(45) Date of Patent: Jan. 22, 2019

(54) METHOD FOR GENERATING PLASMA UNIFORMLY ON DIELECTRIC MATERIAL

(71) Applicant: Research & Business Foundation Sungkyunkwan University, Suwon-si (KR)

(72) Inventors: Dong Geun Jung, Seoul (KR); Yong Ki Cho, Ansan-si (KR); Won Jin Ban, Suwon-si (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 496 days.

(21) Appl. No.: 14/846,048

(22) Filed: Sep. 4, 2015

(65) Prior Publication Data
US 2016/0068960 A1  Mar. 10, 2016

(30) Foreign Application Priority Data
Sep. 5, 2014  (KR) .......................... 10-2014-0119310

(51) Int. Cl.
*C23C 16/50*  (2006.01)
*C23C 16/503*  (2006.01)
(Continued)

(52) U.S. Cl.
CPC .............. *C23C 16/503* (2013.01); *A61F 2/82* (2013.01); *C23C 16/0245* (2013.01);
(Continued)

(58) Field of Classification Search
CPC ................................................... C23C 16/503
See application file for complete search history.

(56) References Cited

U.S. PATENT DOCUMENTS 3,829,629 A * 8/1974 Nitta ...................... H01B 17/42
                                                                174/211
4,219,791 A * 8/1980 Moore .................. H01F 27/323
                                                                174/120 SR
(Continued)

OTHER PUBLICATIONS

Cho, Yong Ki, et al. "Bioactive surgace modifications on inner walls of poly-tetra-fluoro-ethylene tubes using dielectric barrier discharge." *Applied Surface Science* 296 (2014): 79-85. (7 pages, in English).
(Continued)

*Primary Examiner* — Cachet I Sellman
(74) *Attorney, Agent, or Firm* — NSIP Law

(57) ABSTRACT

The present invention relates to a method for checking a discharge inception voltage of a dielectric material, a method for forming a displacement field on the dielectric materials comprising applying a voltage the same as or higher than the discharge inception voltage generated by an external field obtained from the above to the dielectric material to which electrodes are connected, a method for forming plasma on the surfaces of the dielectric material comprising injecting reaction gases and applying a voltage the same as or higher than the discharge inception voltage obtained above to the dielectric material to which electrodes are connected, a method for forming a displacement field on the entire surface of the dielectric material comprising applying a voltage the same as or higher than the discharge inception voltage obtained above to the dielectric material to which electrodes are connected, and a dielectric material which is modified, in which the surfaces thereof are treated with plasma by the methods described above.

16 Claims, 32 Drawing Sheets

(51) Int. Cl.
   *C23C 16/52* (2006.01)
   *A61F 2/82* (2013.01)
   *C23C 16/02* (2006.01)
   *C23C 16/04* (2006.01)
   *H05H 1/24* (2006.01)
   *G01R 31/12* (2006.01)

(52) U.S. Cl.
   CPC ............ *C23C 16/045* (2013.01); *C23C 16/52* (2013.01); *H05H 1/2406* (2013.01); *A61F 2240/001* (2013.01); *G01R 31/1263* (2013.01); *H05H 2001/2412* (2013.01); *H05H 2001/2456* (2013.01); *H05H 2001/2462* (2013.01)

(56) References Cited

U.S. PATENT DOCUMENTS

| | | | | |
|---|---|---|---|---|
| 4,654,546 A | * | 3/1987 | Kirjavainen | H04R 23/00 29/594 |
| 4,751,488 A | * | 6/1988 | Lanoue | H01B 3/308 336/84 R |
| 4,918,468 A | * | 4/1990 | Miekka | G03G 15/323 347/126 |
| 5,185,556 A | * | 2/1993 | Yagi | H01J 17/04 313/620 |
| 2005/0157446 A1 | * | 7/2005 | Brubaker | H01G 2/14 361/301.5 |
| 2006/0213865 A1 | * | 9/2006 | Honda | H01J 37/32522 216/67 |
| 2009/0003859 A1 | * | 1/2009 | Kagawa | G03G 15/0291 399/50 |
| 2009/0248328 A1 | * | 10/2009 | Younsi | G01R 31/343 702/59 |
| 2013/0014971 A1 | * | 1/2013 | Muto | H01B 3/301 174/110 SR |
| 2015/0263489 A1 | * | 9/2015 | Otsubo | H01T 2/02 361/56 |

OTHER PUBLICATIONS

Cho, Yong Ki, et al. "Hydrophilic surface modification for inner wall of polyethylene tubes using micro plasma." (2016): (3 pages, in Korean with English translation).

Korean Office Action dated Aug. 22, 2016 in counterpart Korean Patent Application No. 10-2014-0119310 (8 pages, in Korean).

* cited by examiner

[FIG. 1]
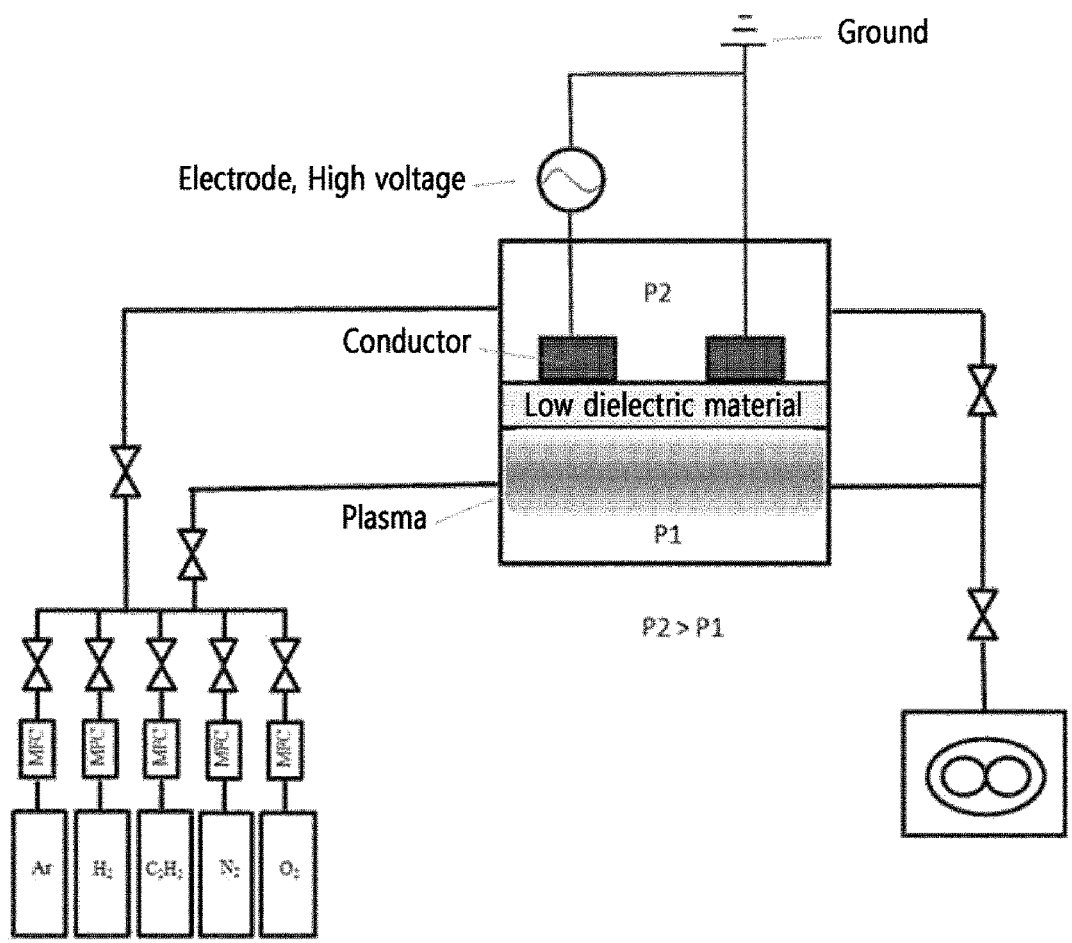

[FIG. 2]
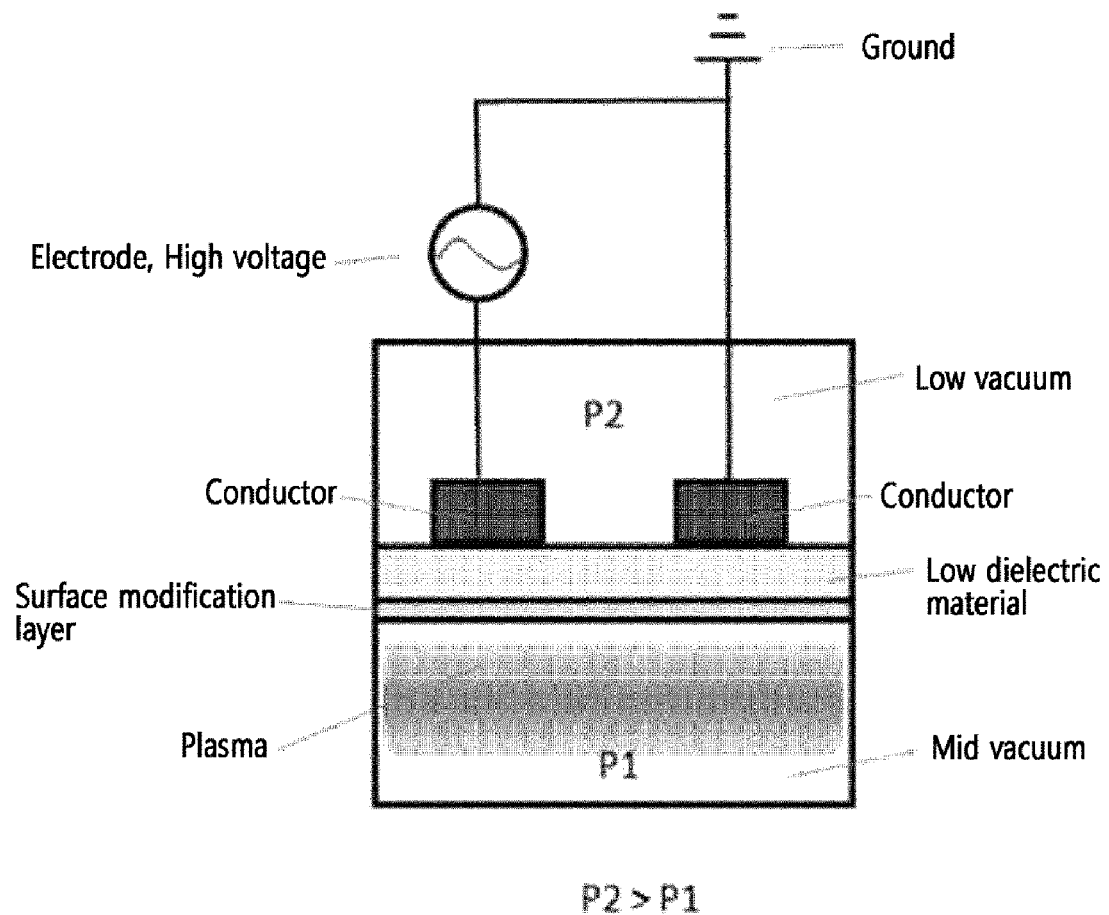

[FIG. 3]
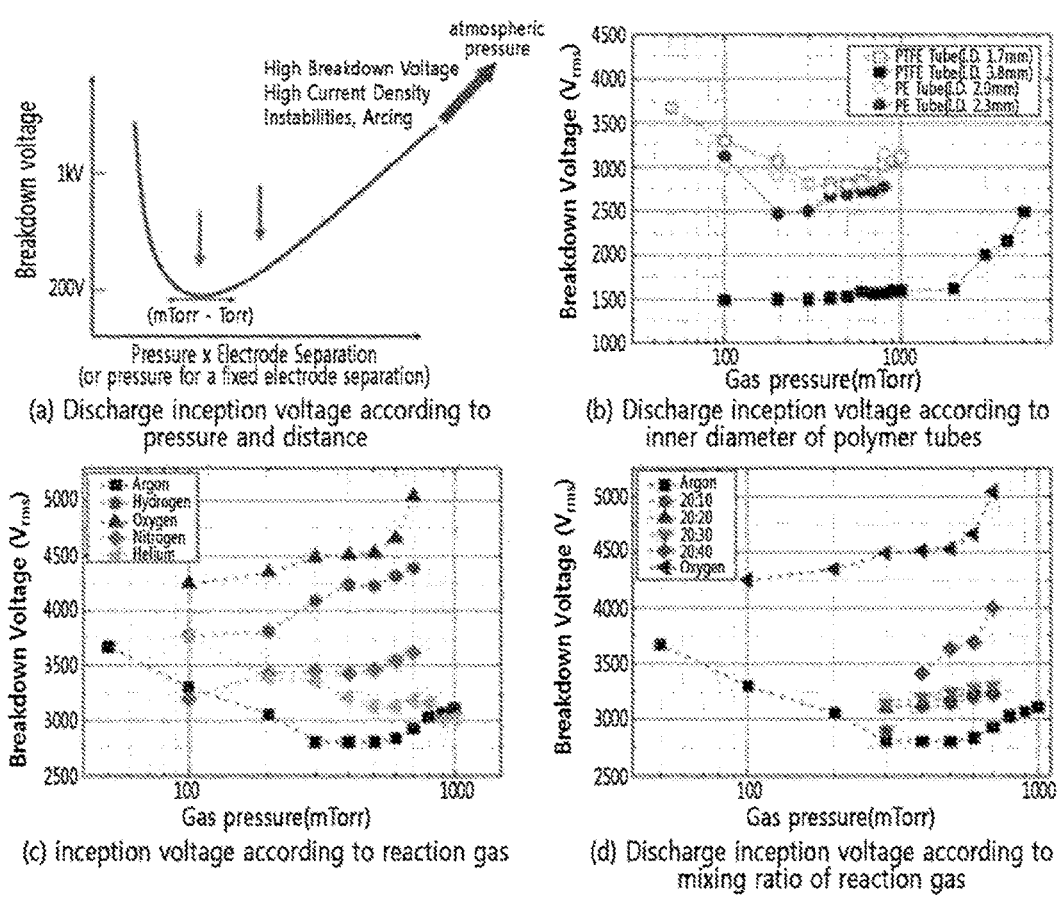

[FIG. 4]
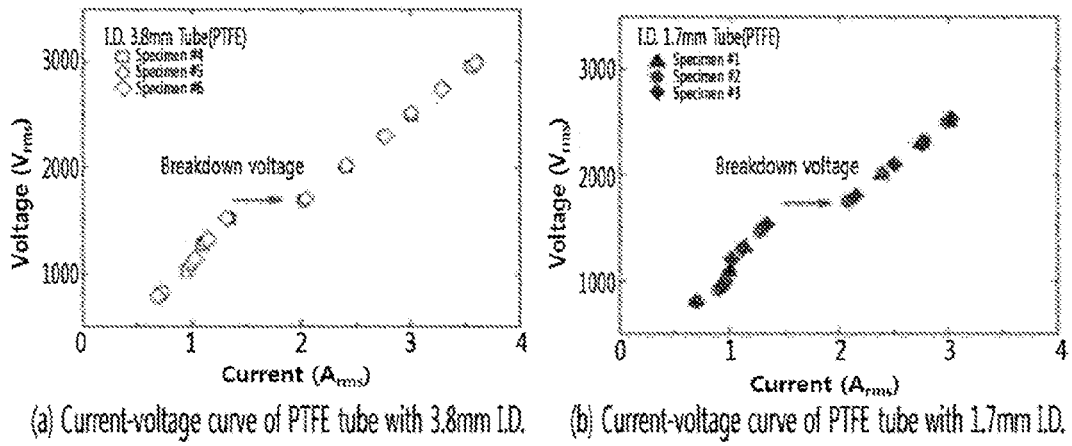
(a) Current-voltage curve of PTFE tube with 3.8mm I.D.    (b) Current-voltage curve of PTFE tube with 1.7mm I.D.
[FIG. 5]
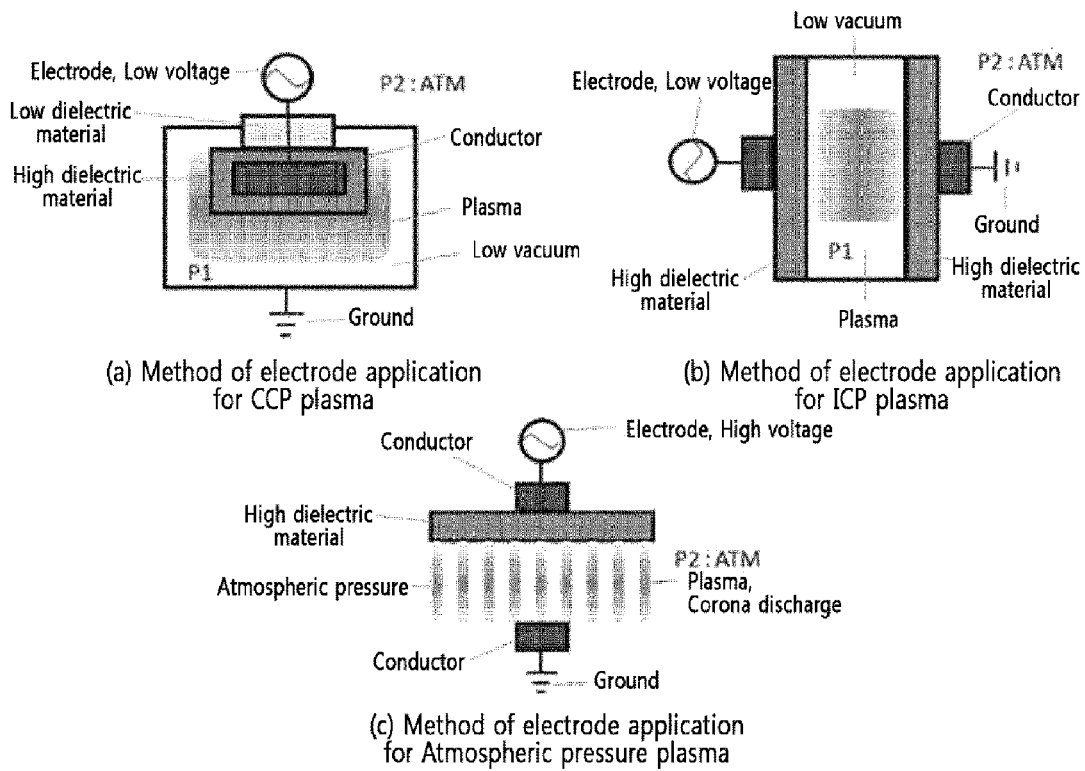
(a) Method of electrode application for CCP plasma
(b) Method of electrode application for ICP plasma
(c) Method of electrode application for Atmospheric pressure plasma

[FIG. 6]
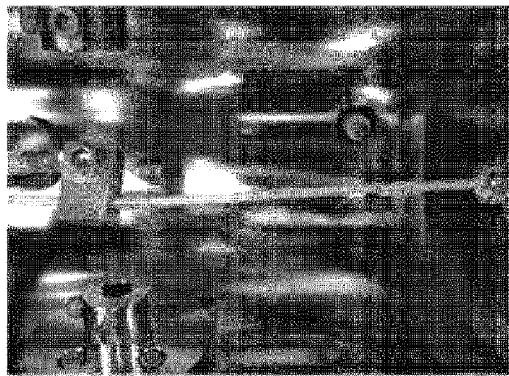    
(a) Discharge of single tube    (b) Discharge of bundle of tubes

[FIG. 7]
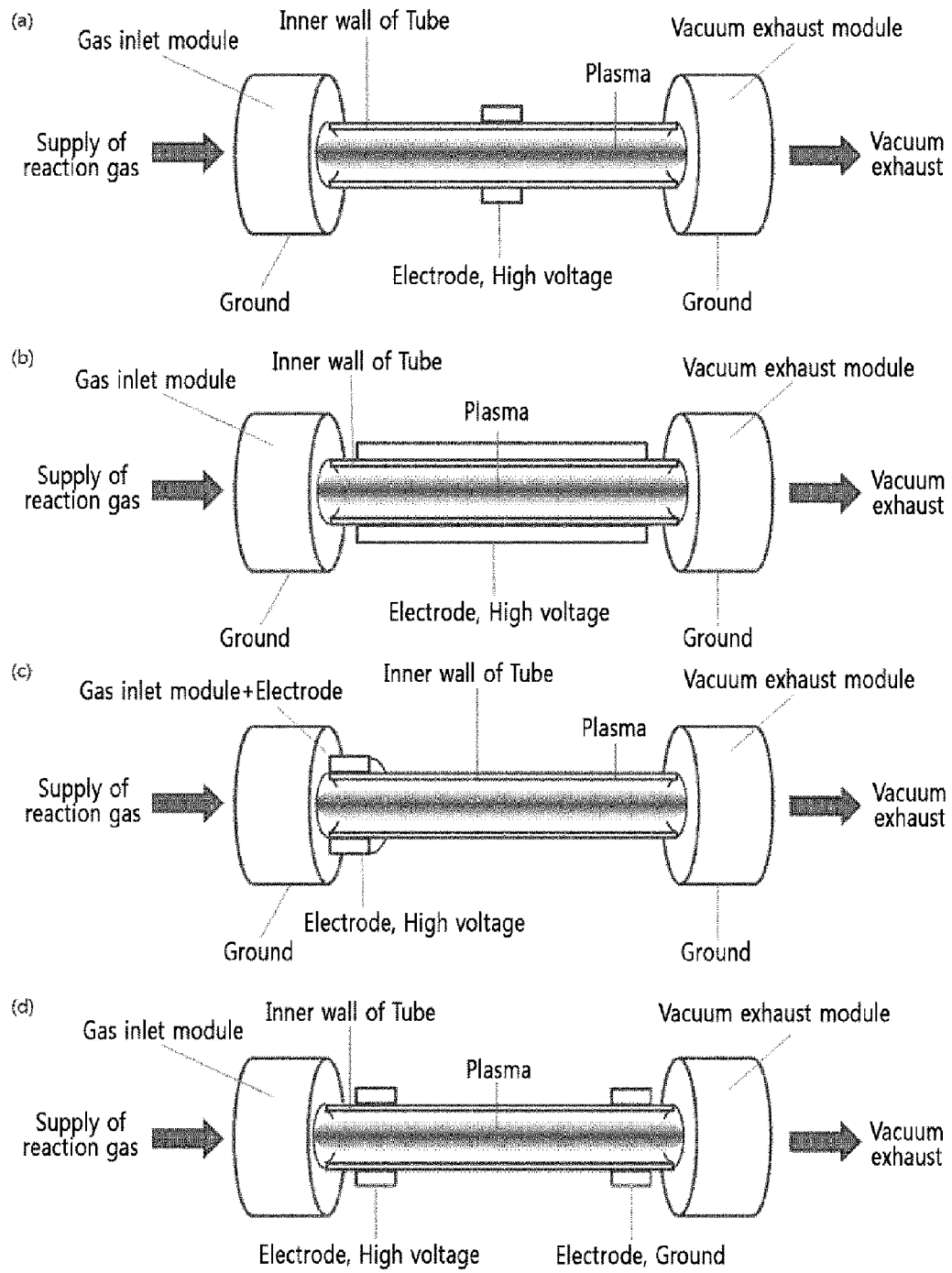

[FIG. 8]
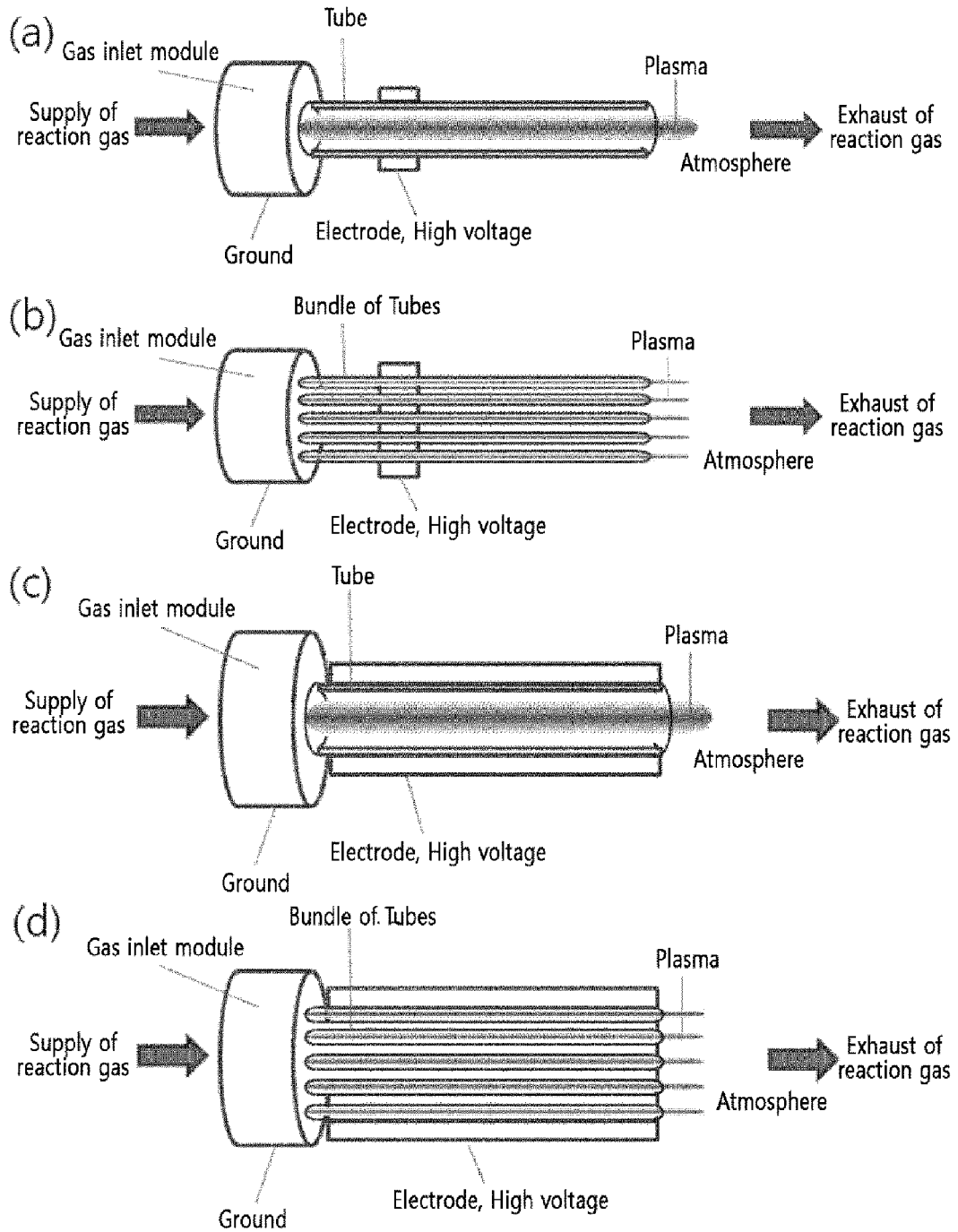

[FIG. 9]
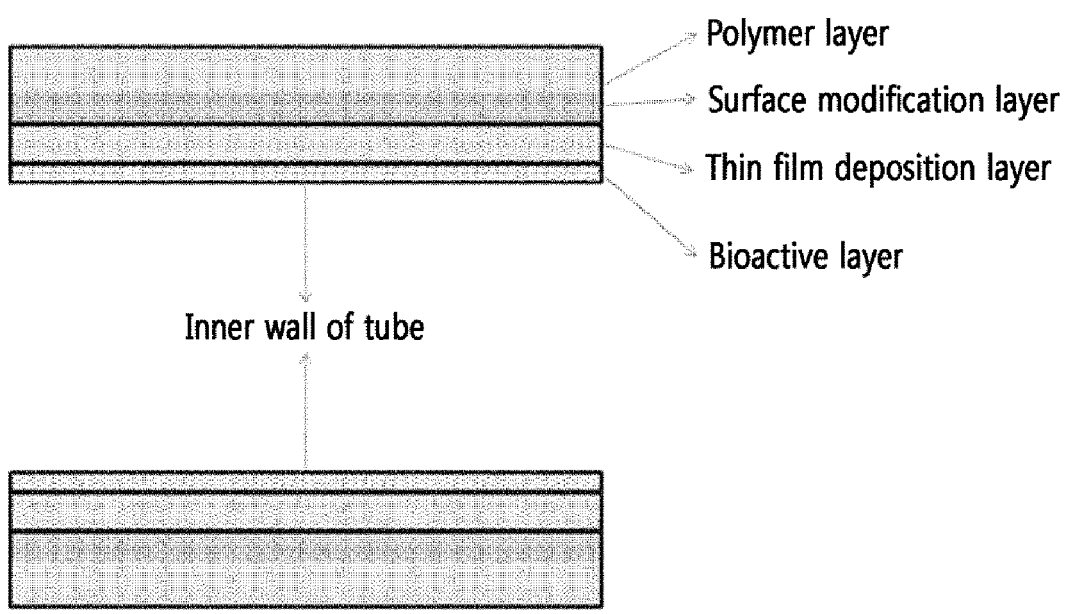

[FIG. 10]
X 1500           X 4000
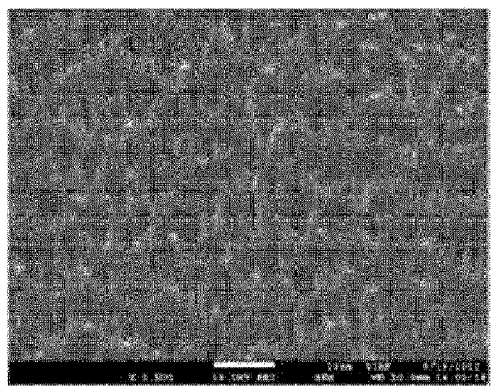
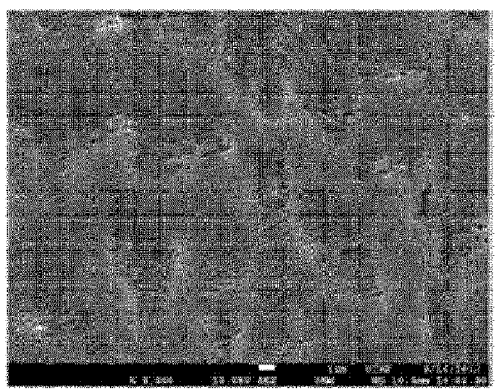
PTFE           PTFE
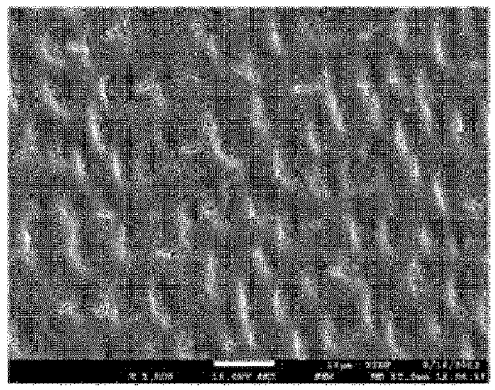
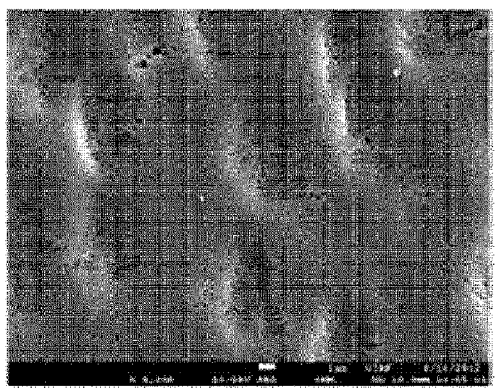
$H_2$ treatment       $H_2$ treatment

[FIG. 11]
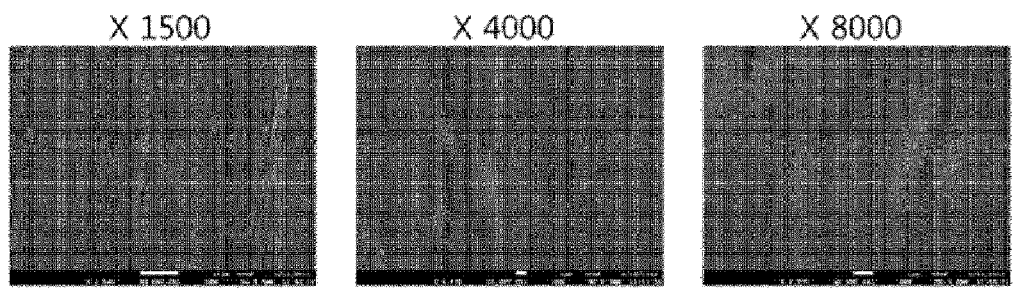
[FIG. 12]
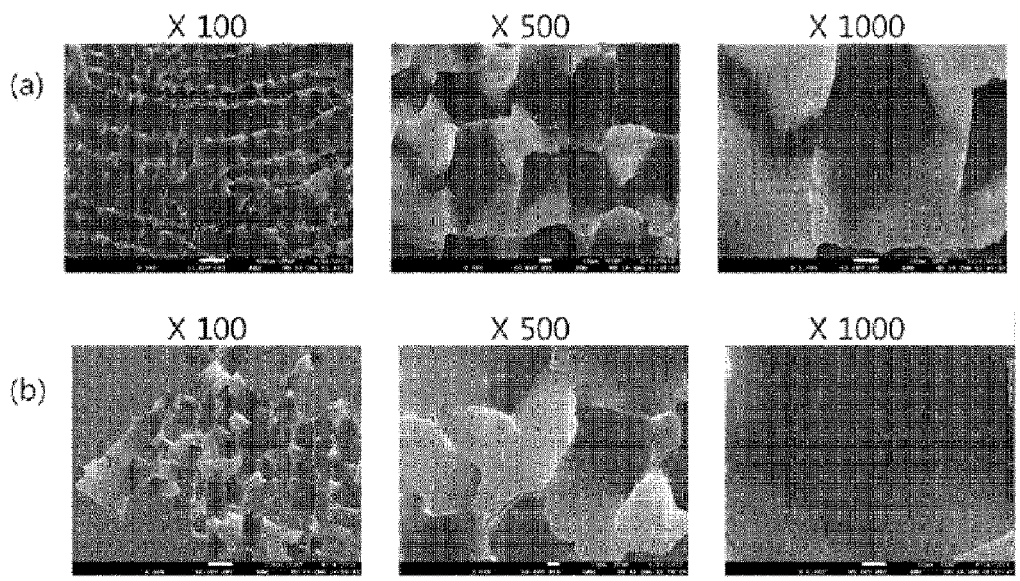

[FIG. 13]
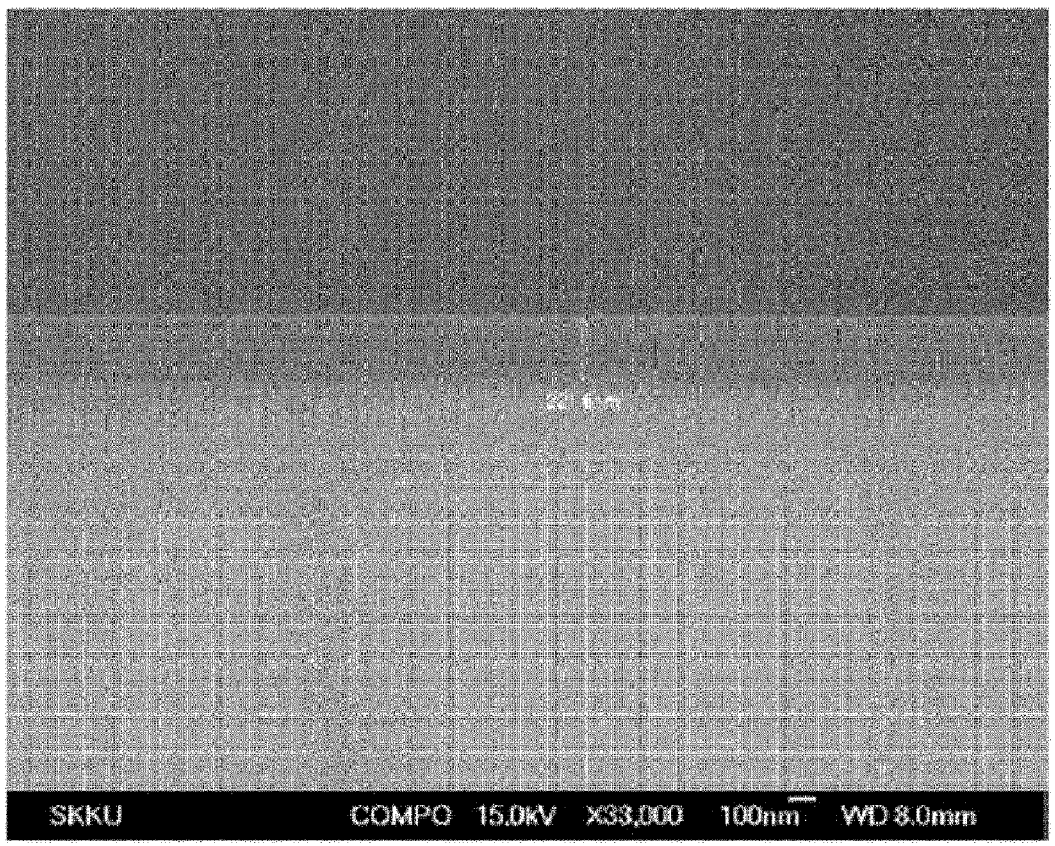

[FIG. 14]
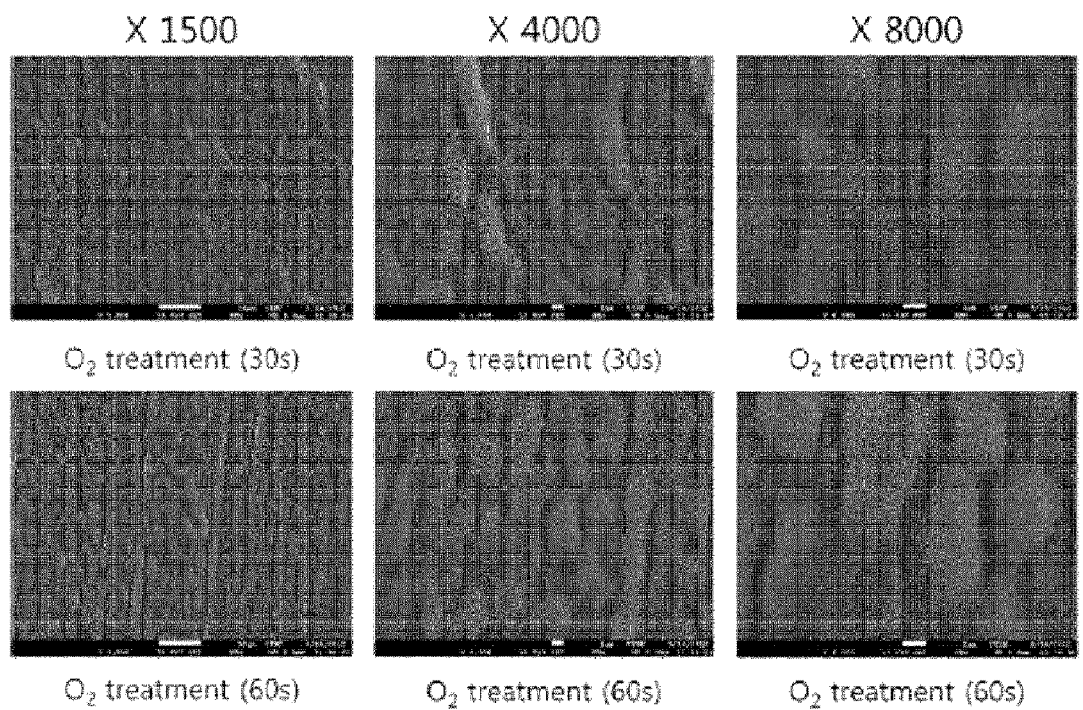

[FIG. 15]
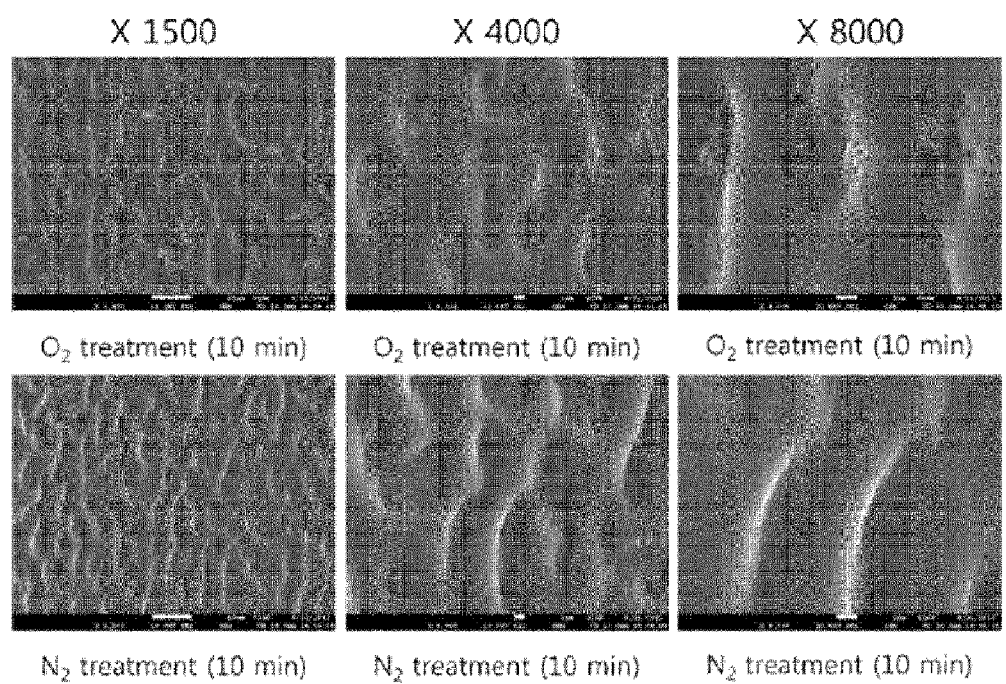

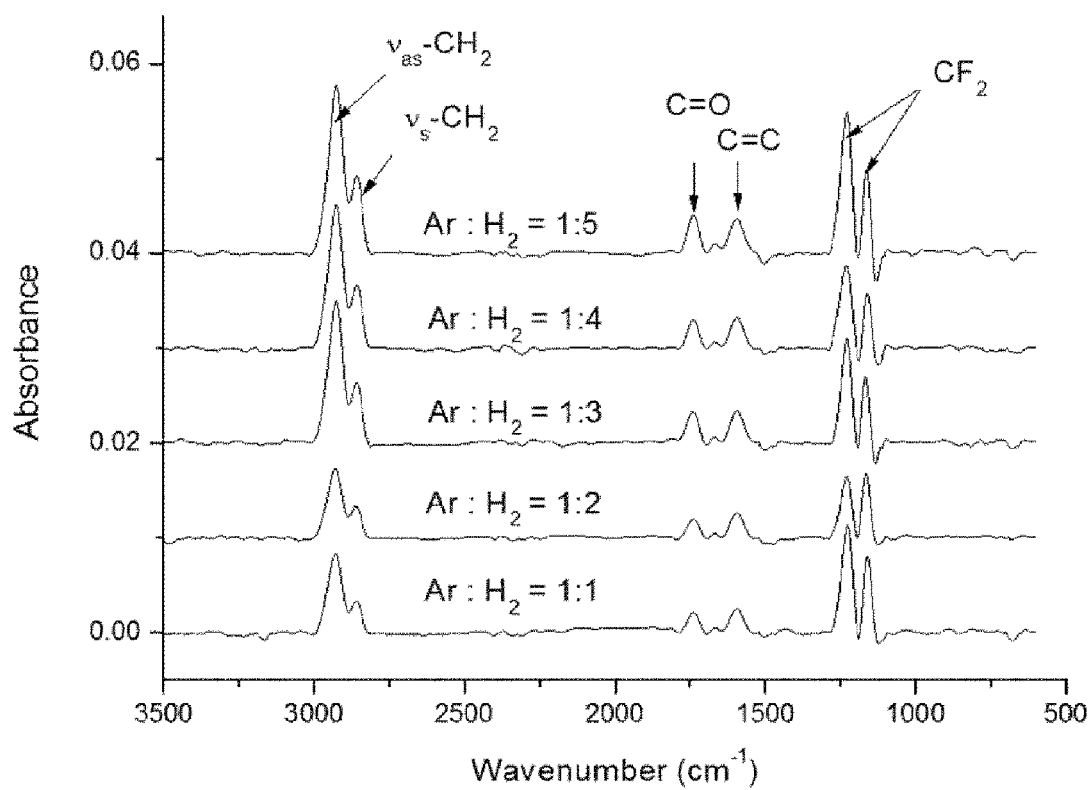
[FIG. 16]

[FIG. 17]
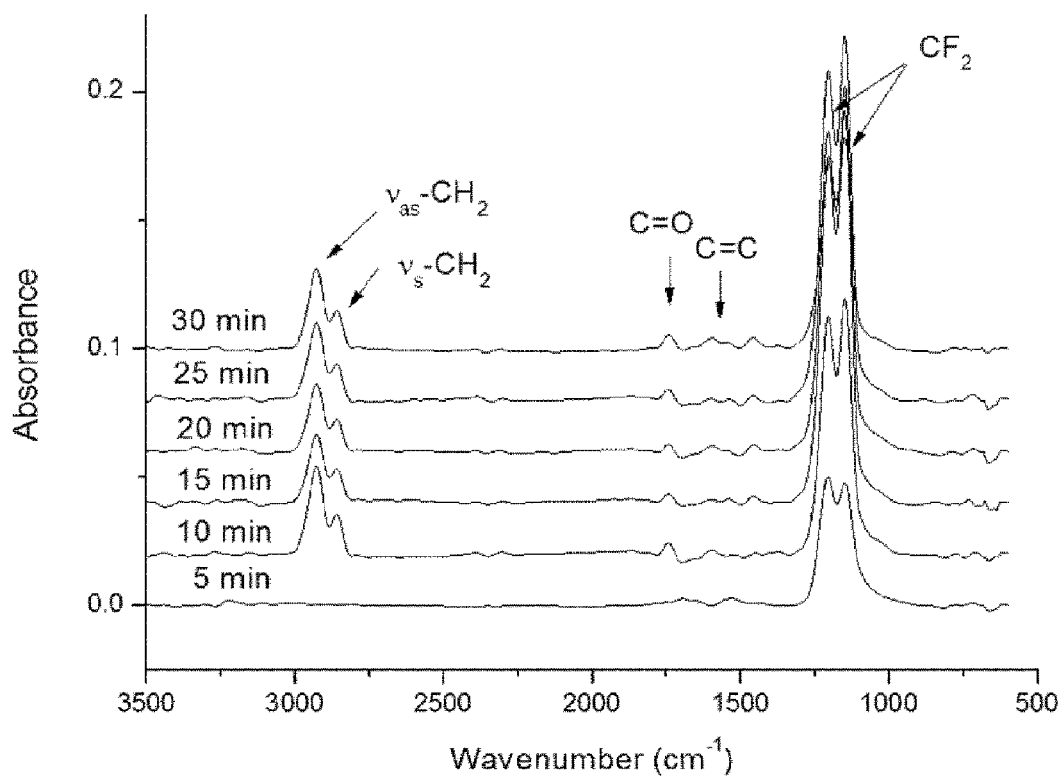

[FIG. 18]
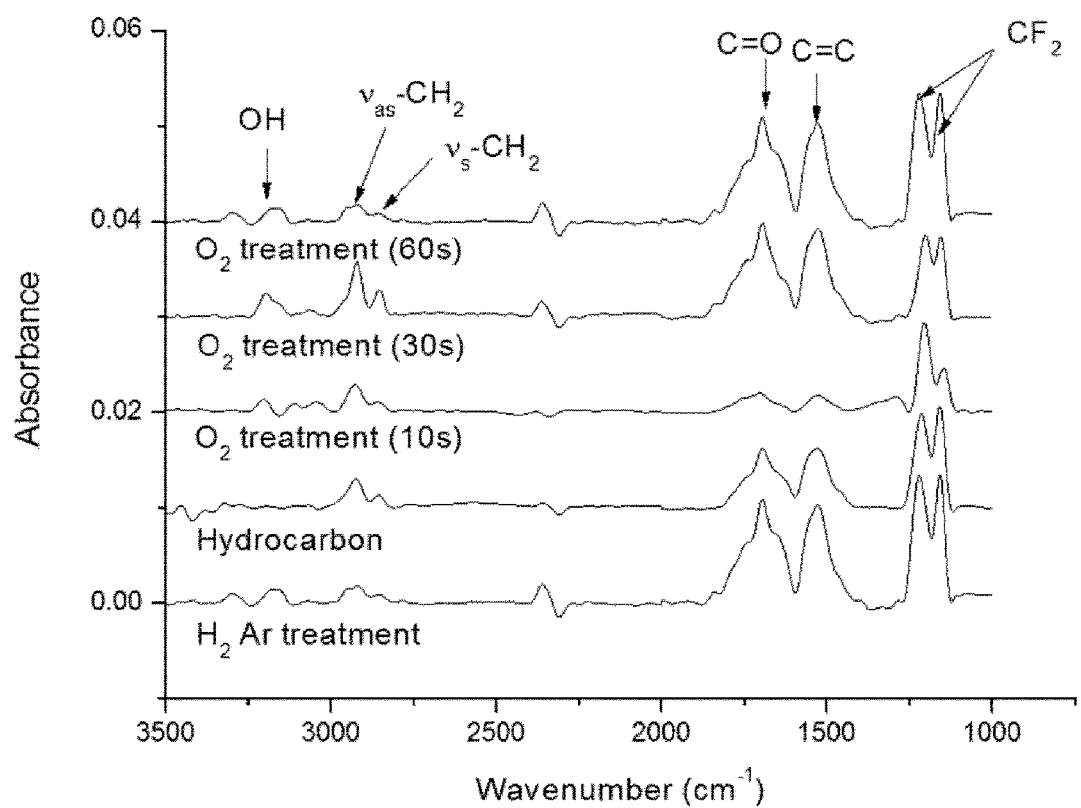

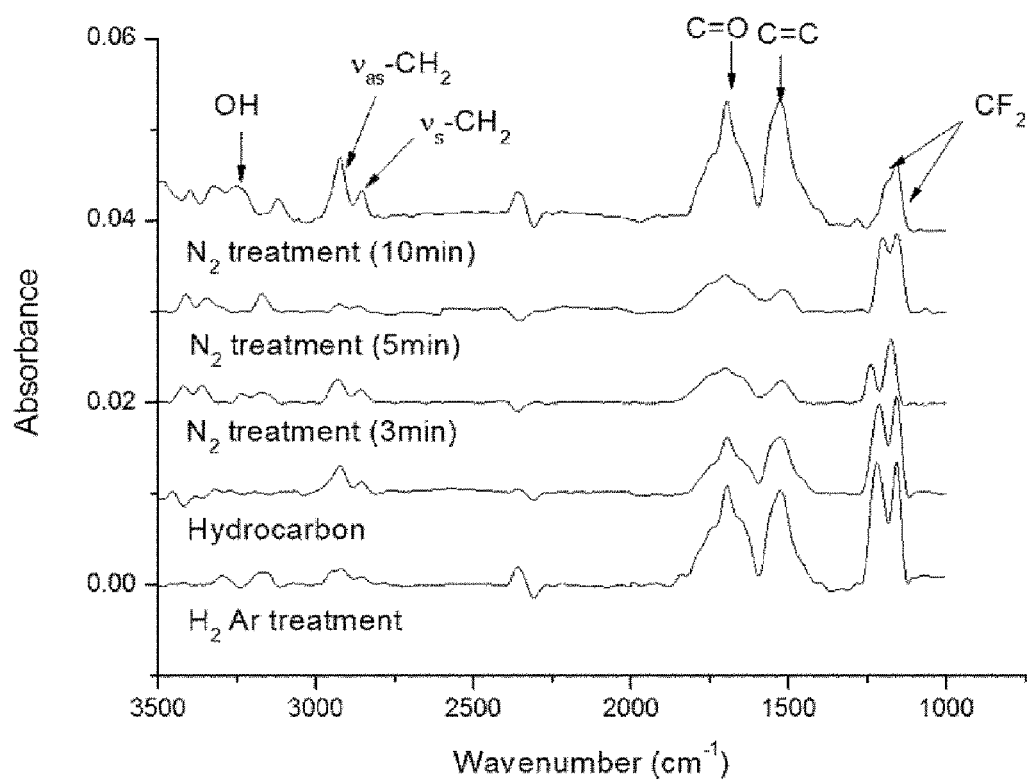
[FIG. 19]

【FIG. 20】
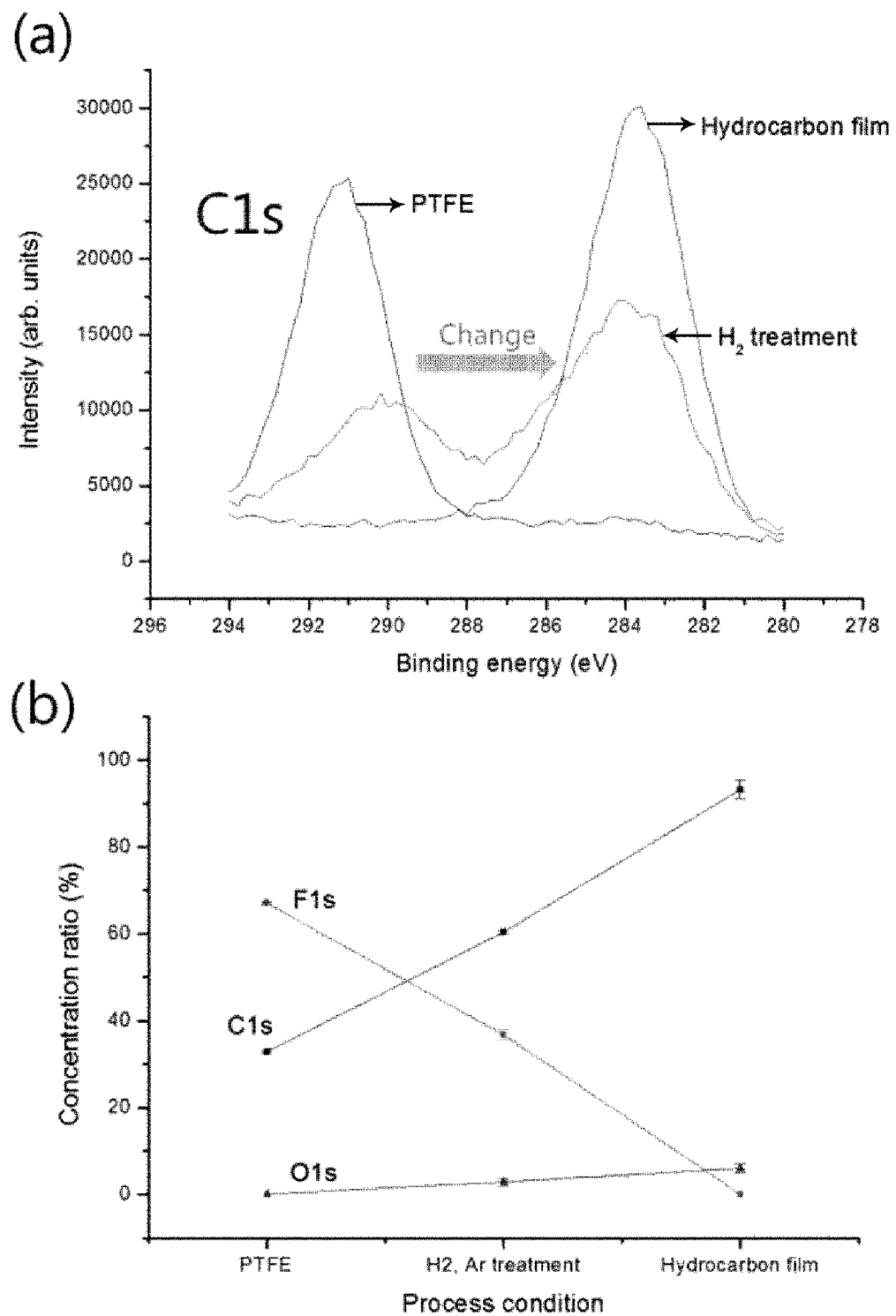

[FIG. 21]
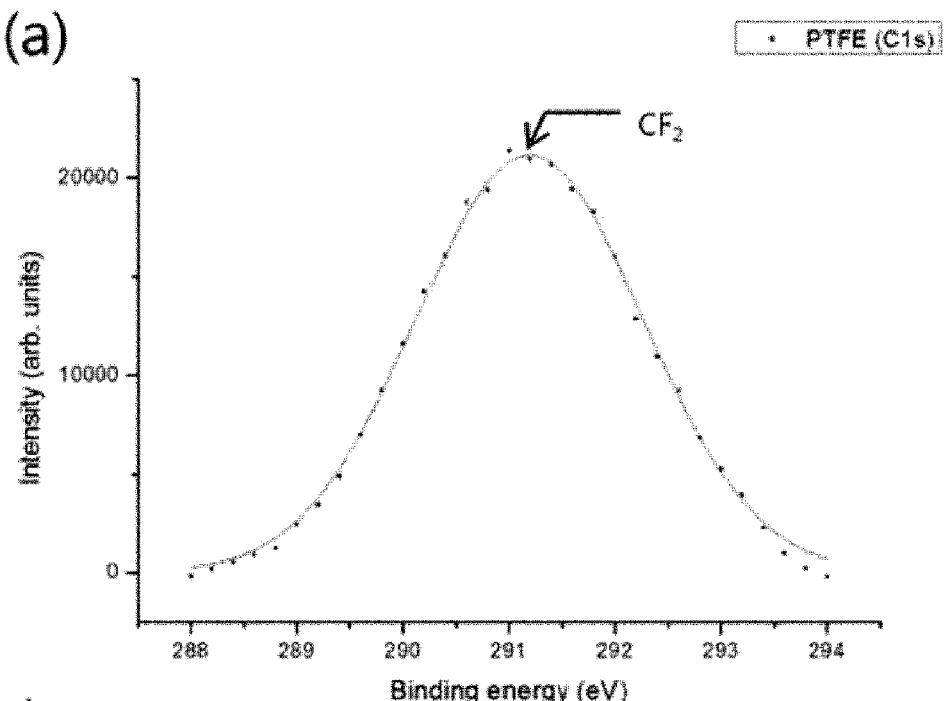
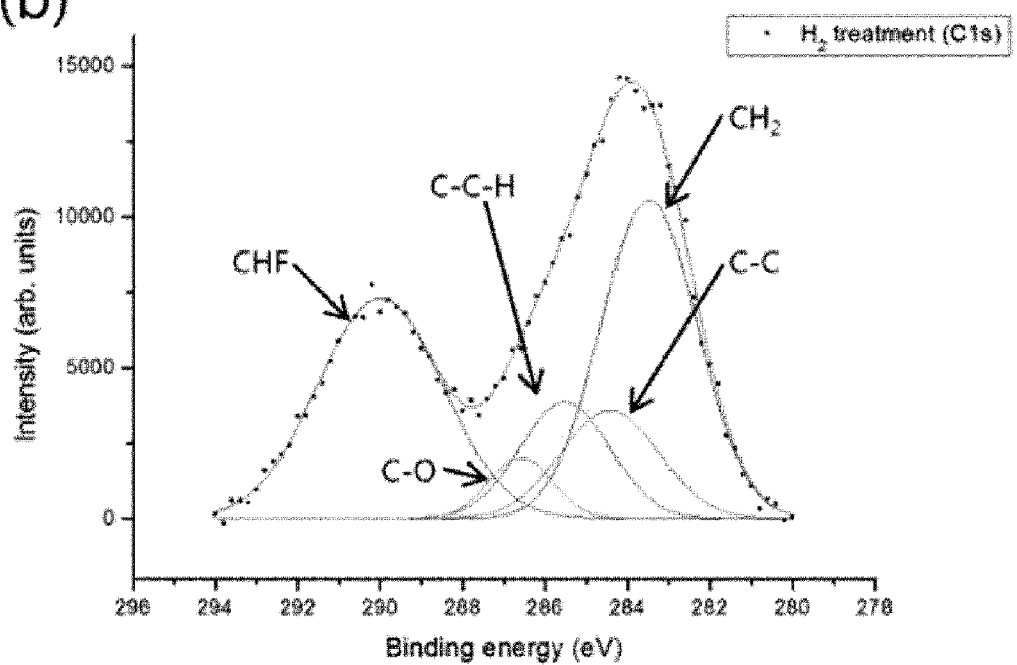

[FIG. 22]
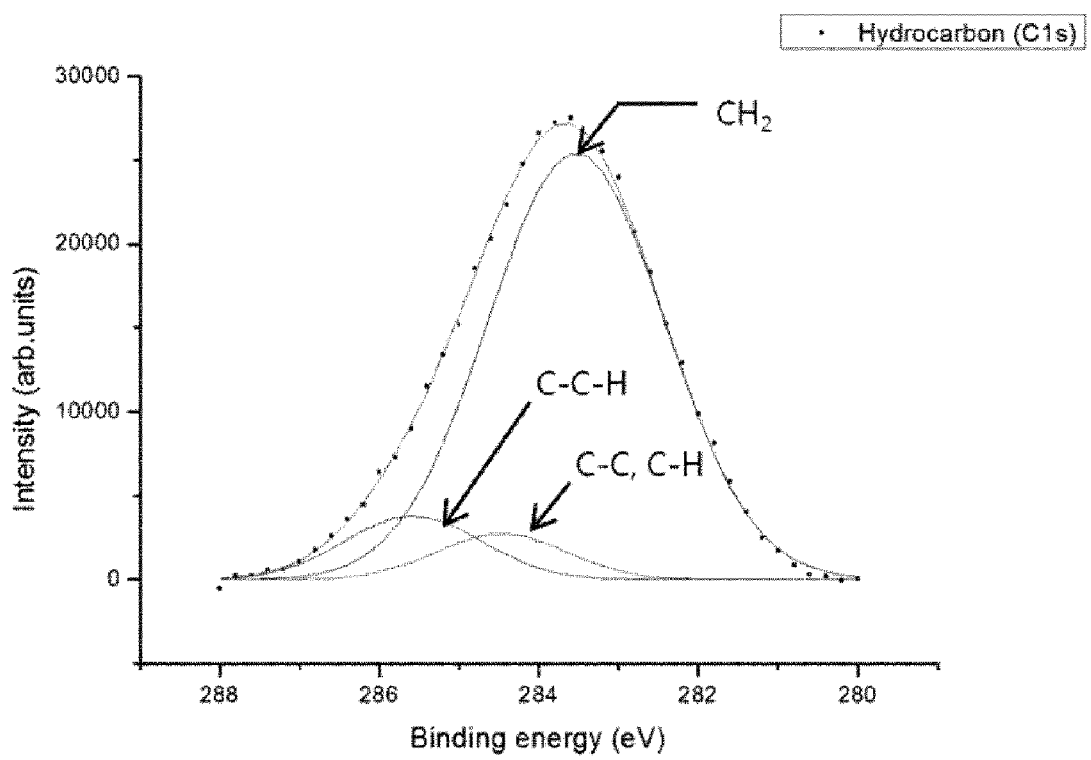

[FIG. 23]
(a)
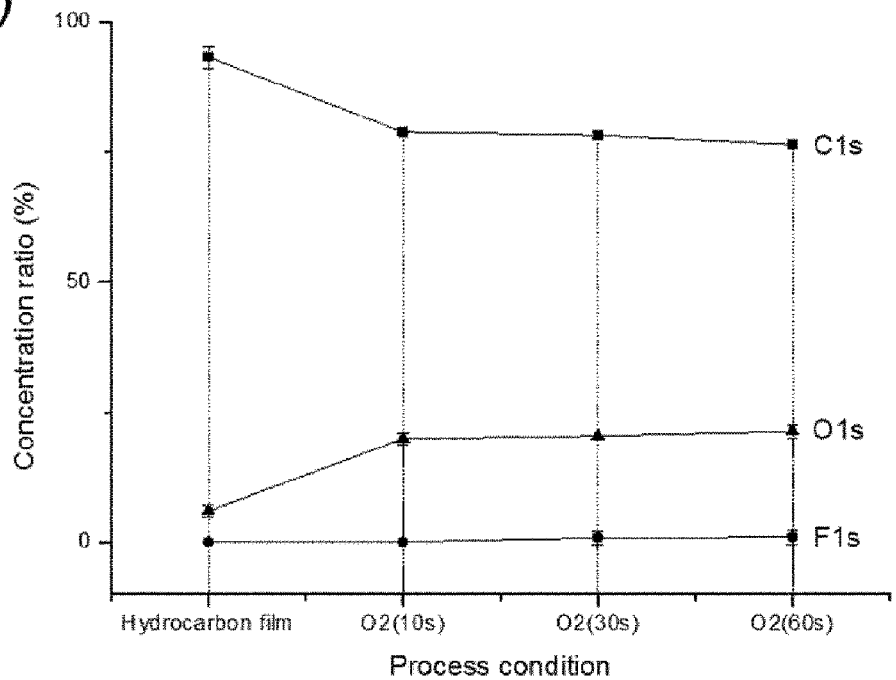
(b)
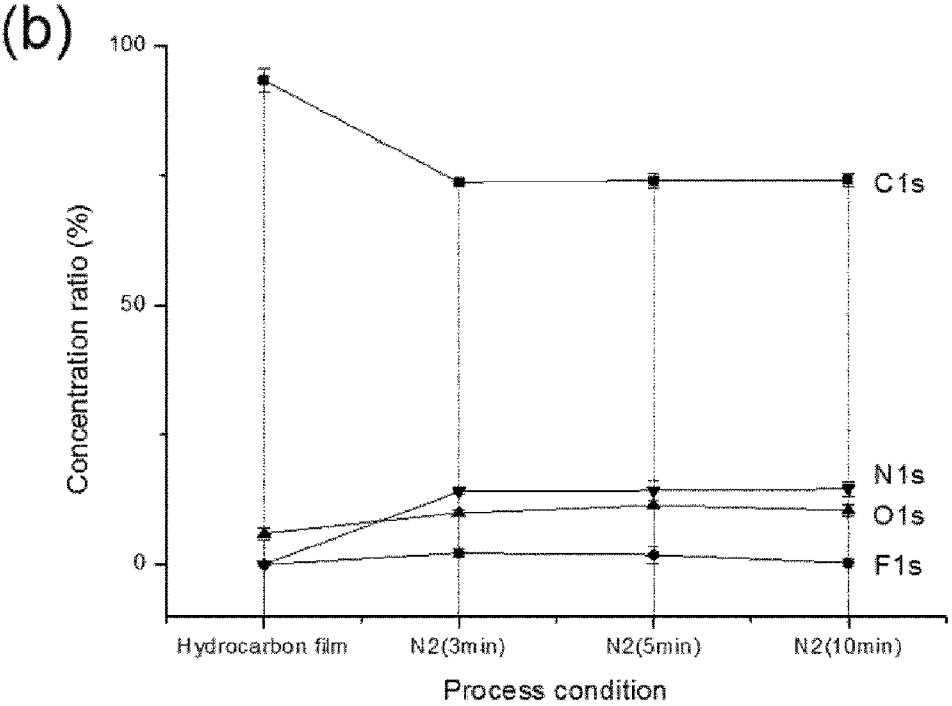

[FIG. 24]
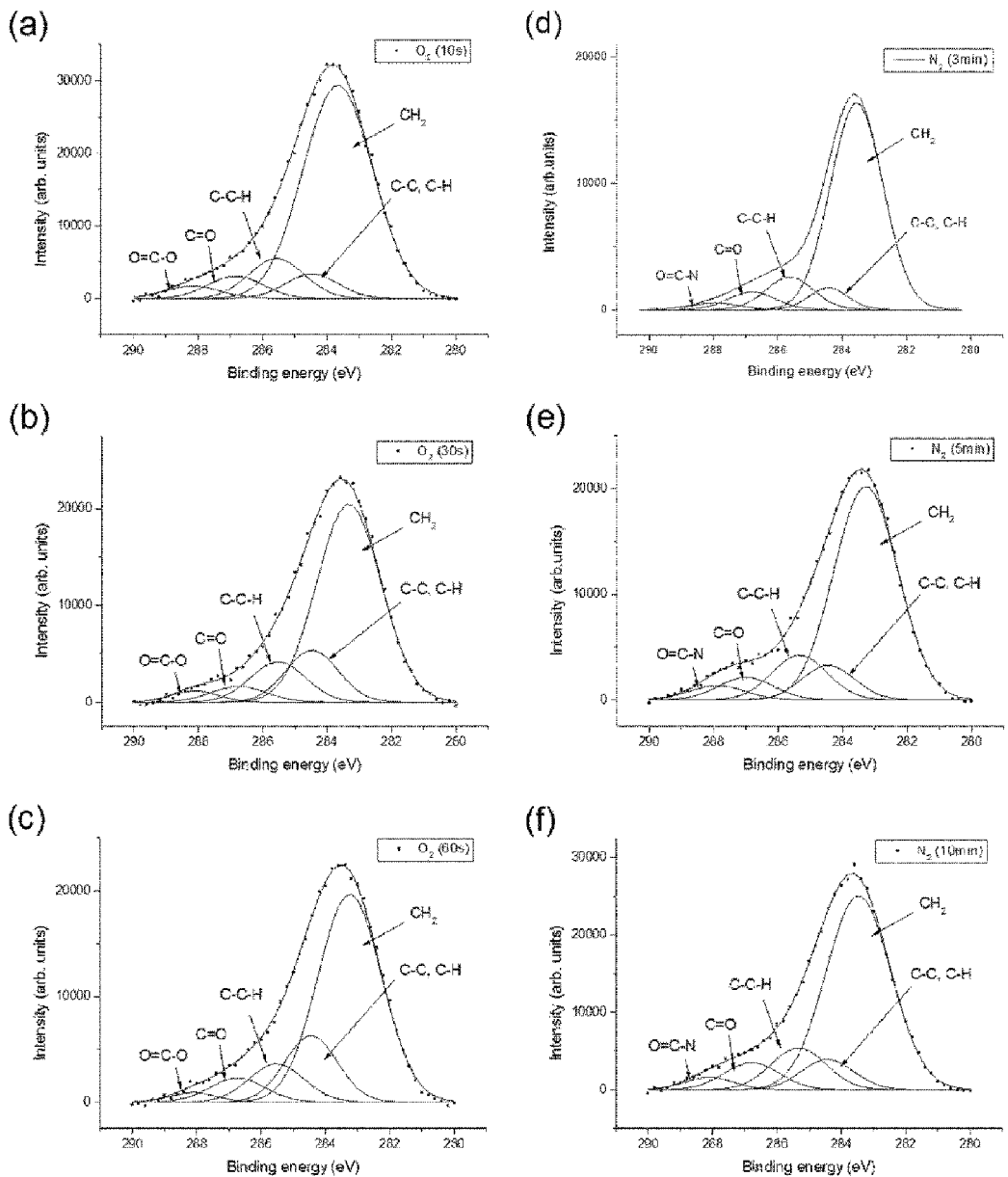

[FIG. 25]
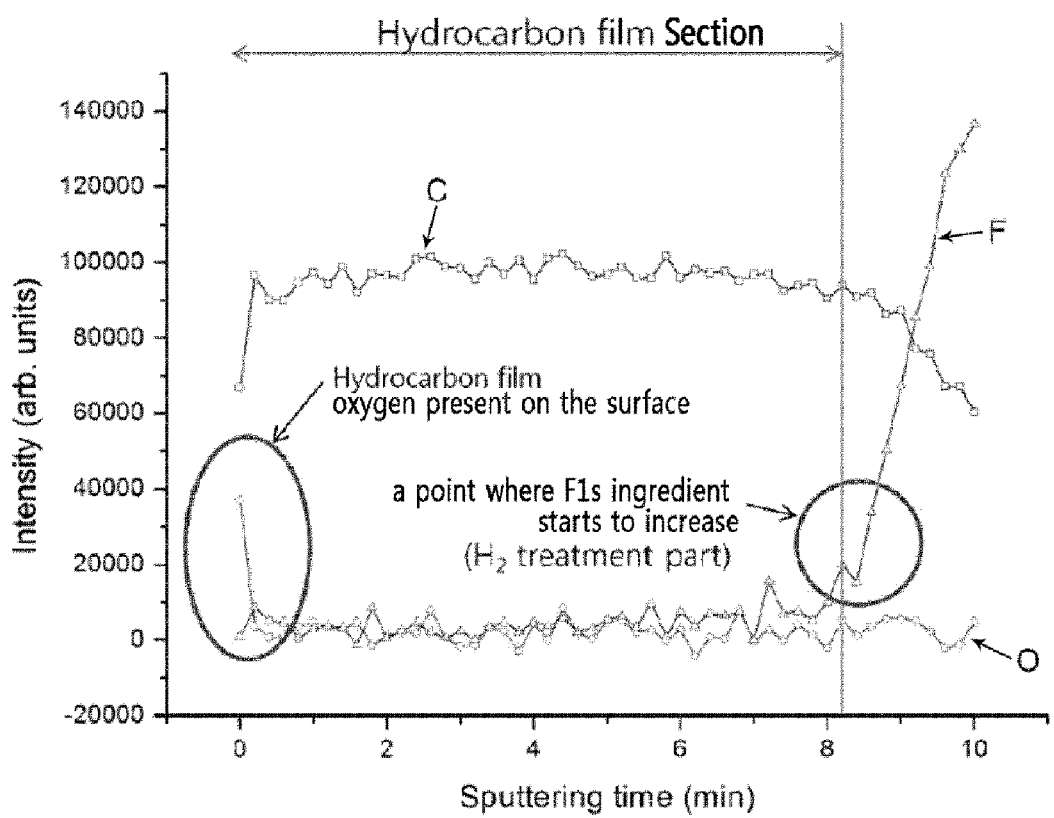

[FIG. 26]
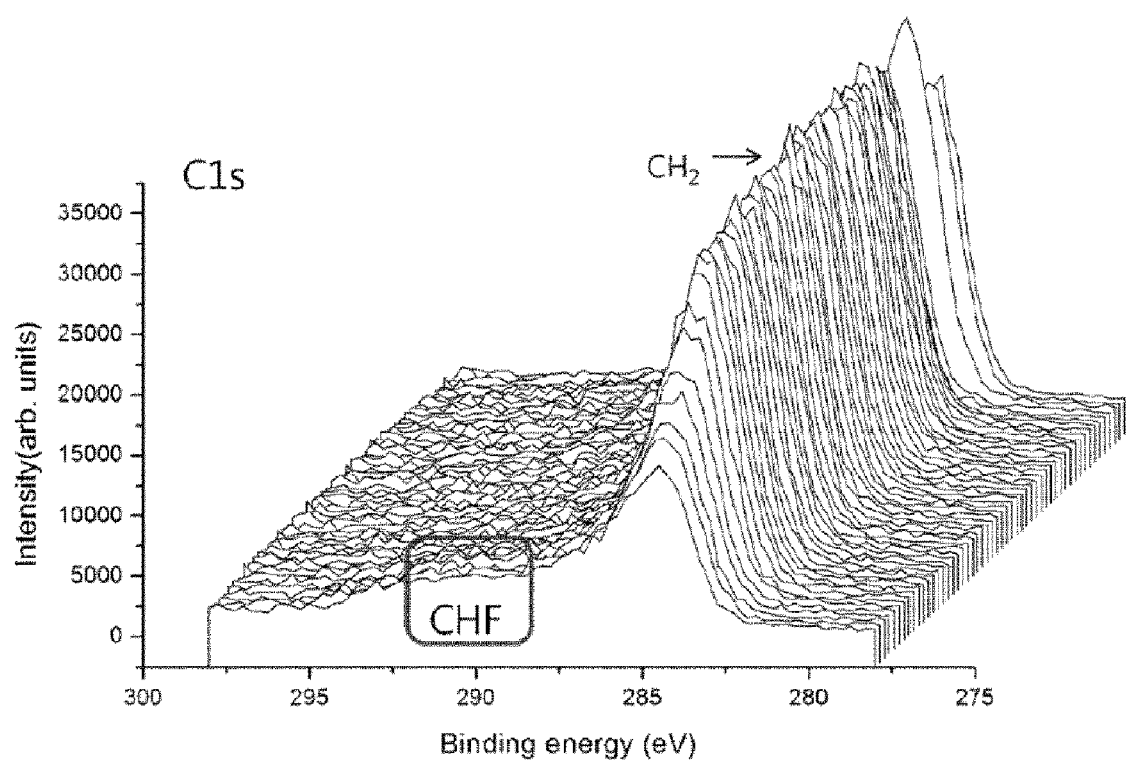

[FIG. 27]
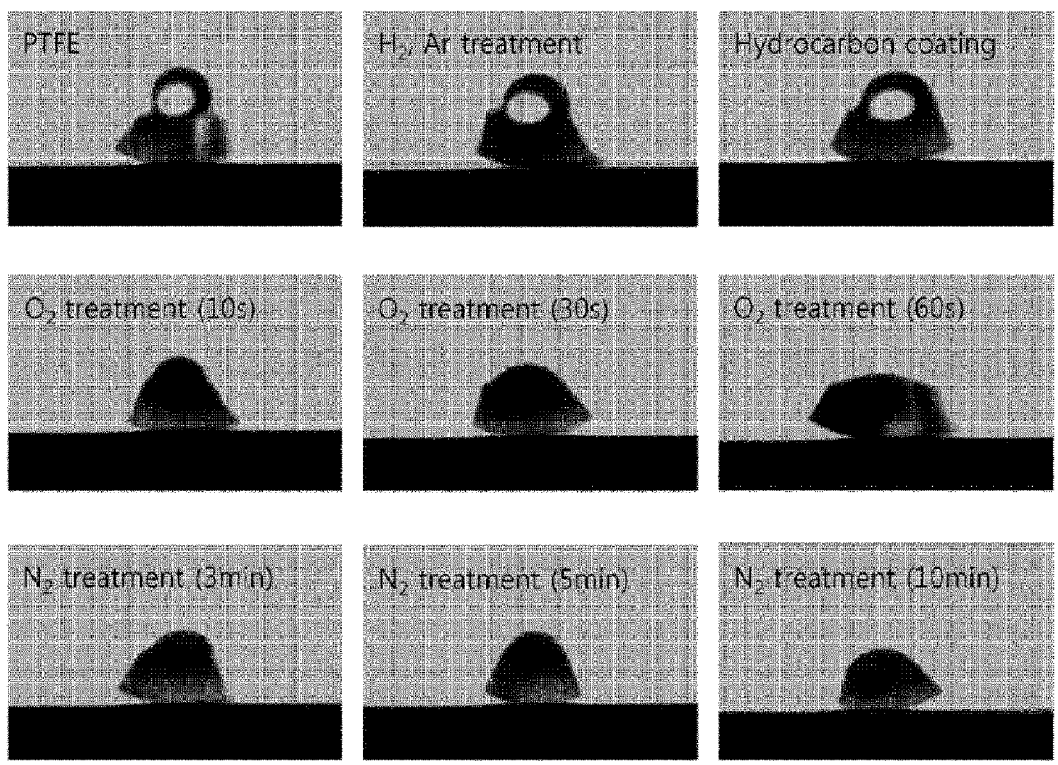

[FIG. 28]
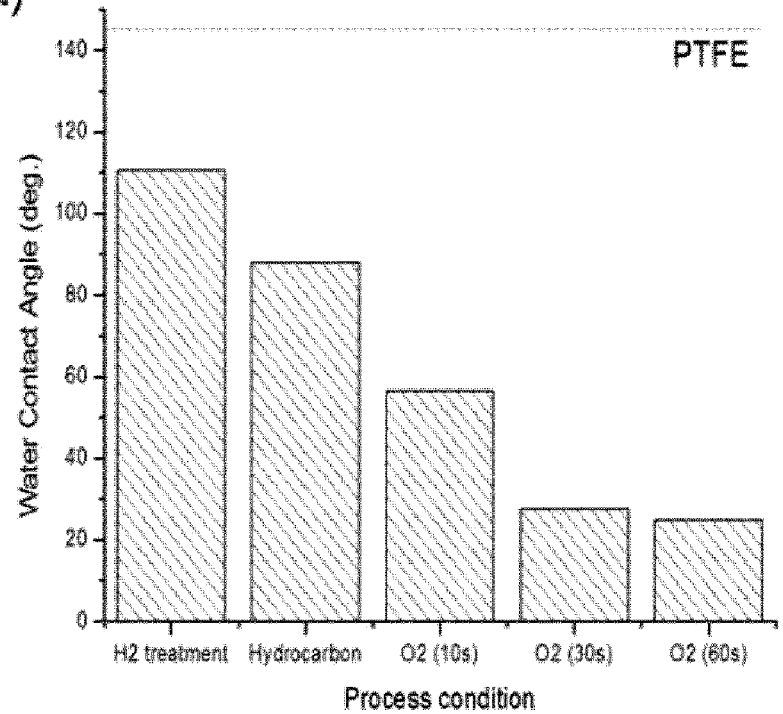
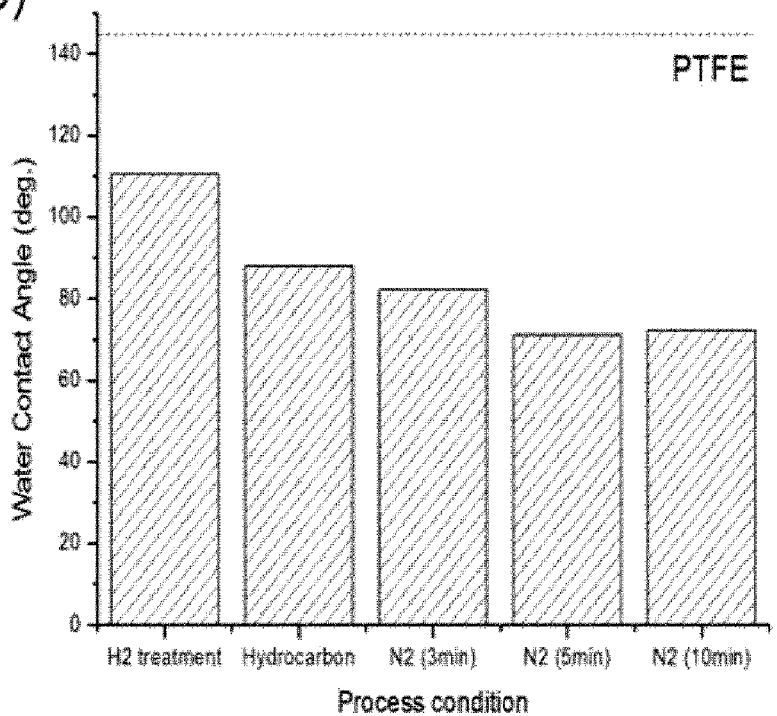

[FIG. 29]
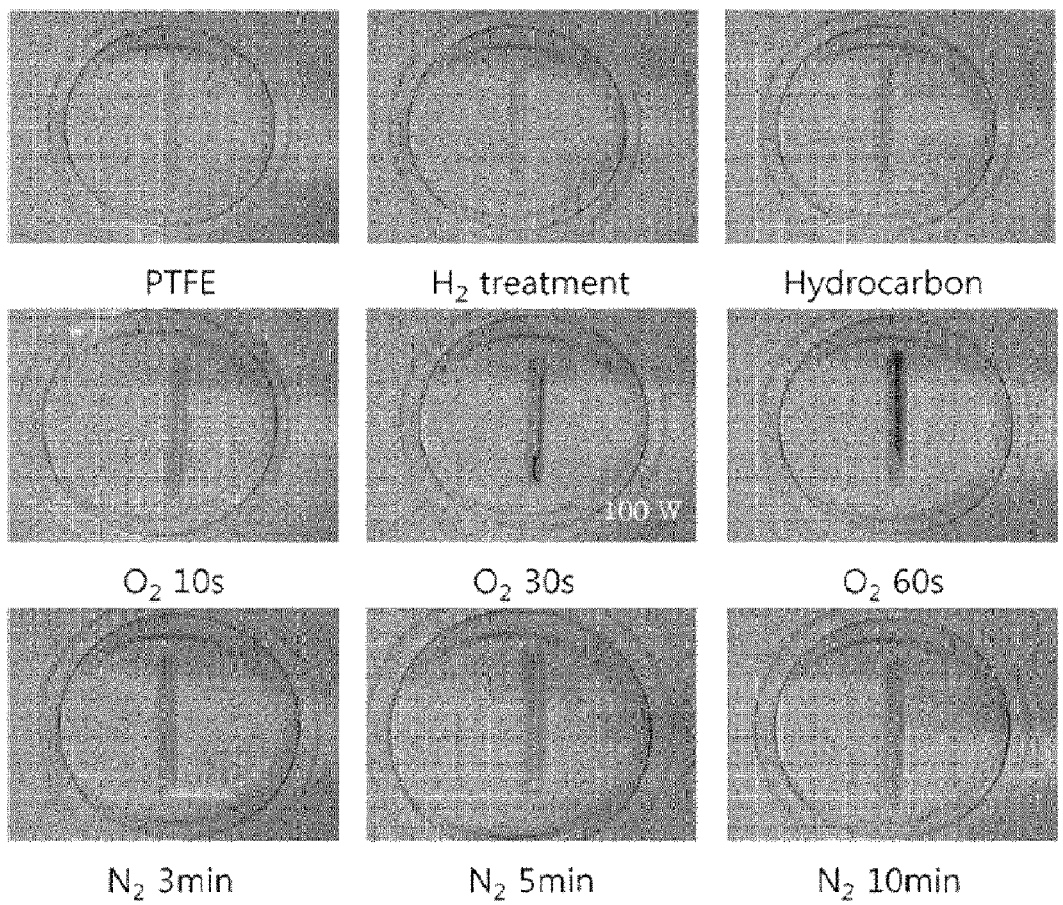

[FIG. 30]
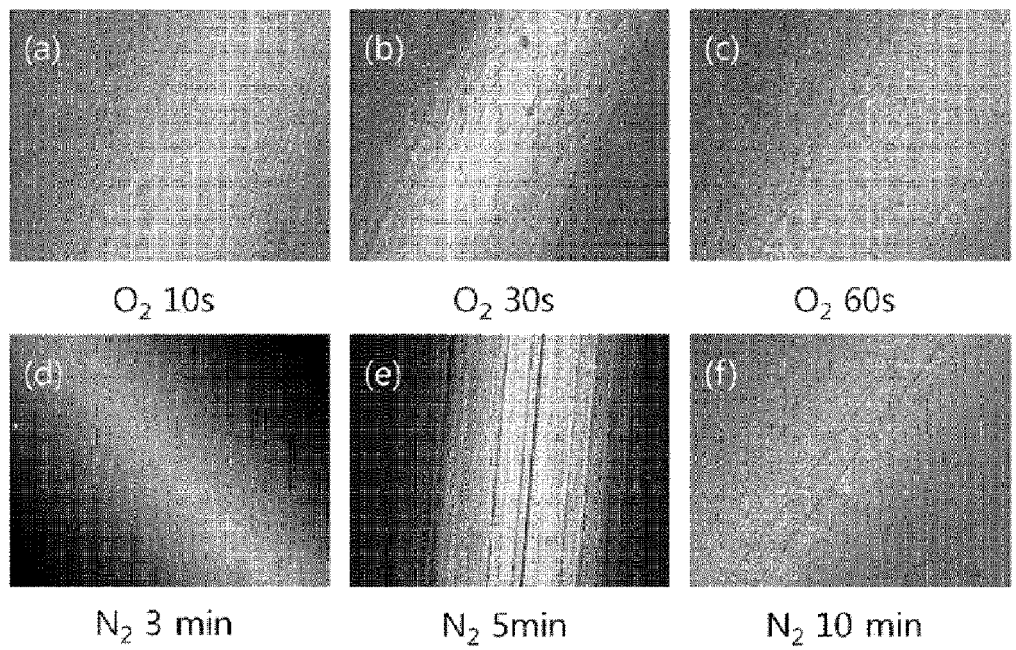
[FIG. 31]
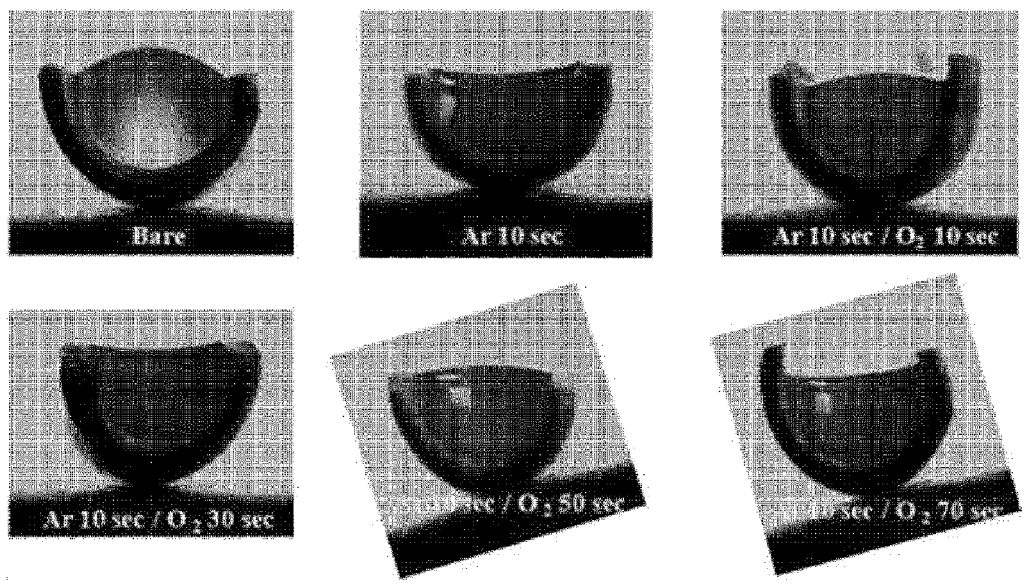

[FIG. 32]
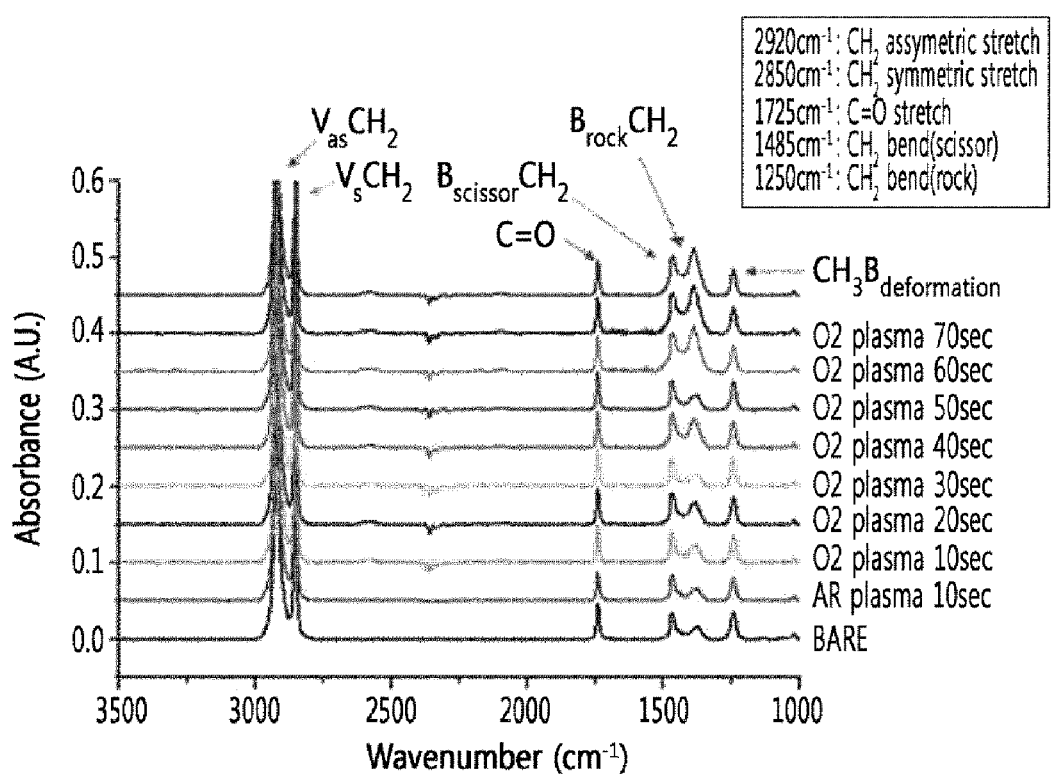

[FIG. 33]
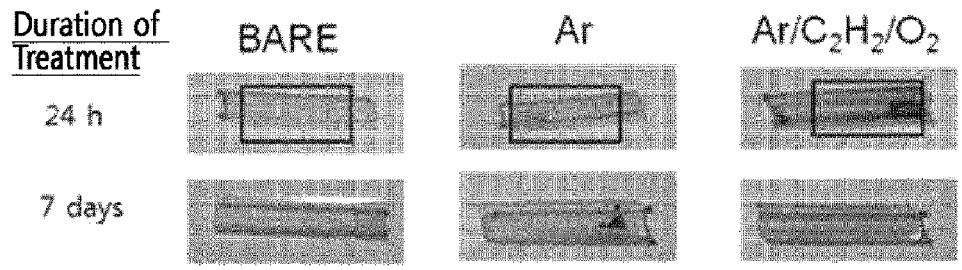
(a) Protein (albumin) adsorption on Polyethylene (PE) tube
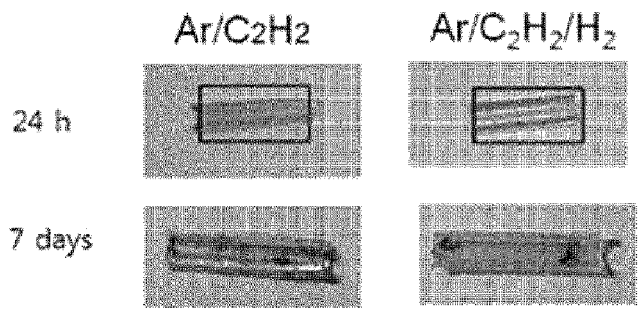
(b) Inhibition of protein (albumin) adsorption on Polyethylene (PE) tube
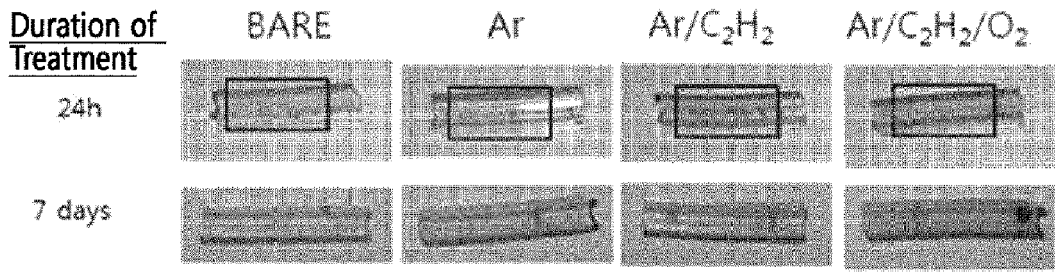
(c) Protein (albumin) adsorption on Polytetrafluoroethylene (PTFE) tube
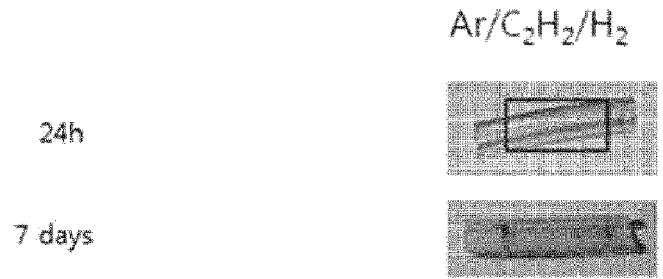
(d) Inhibition of protein (albumin) adsorption on Polytetrafluoroethylene (PTFE) tube

[FIG. 34]
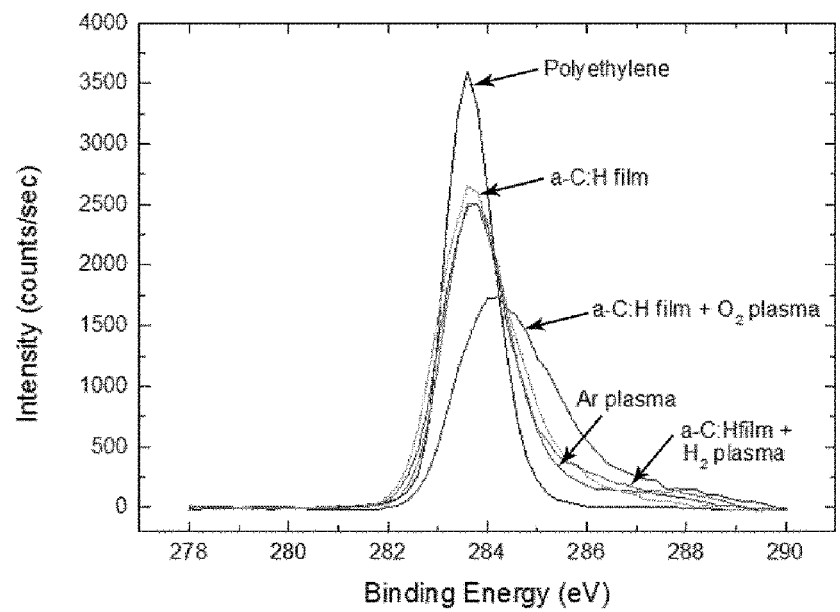
(a) PE Tube
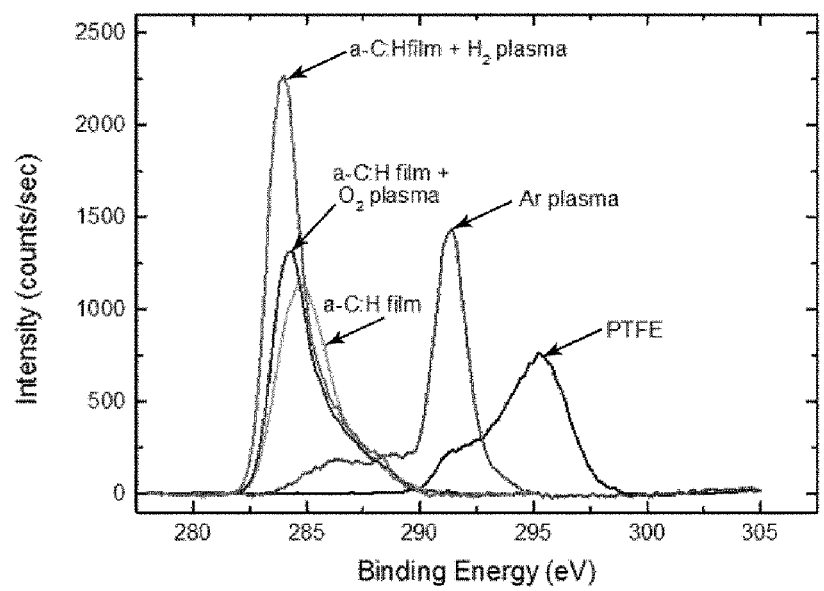
(b) PTFE Tube

[FIG. 35]
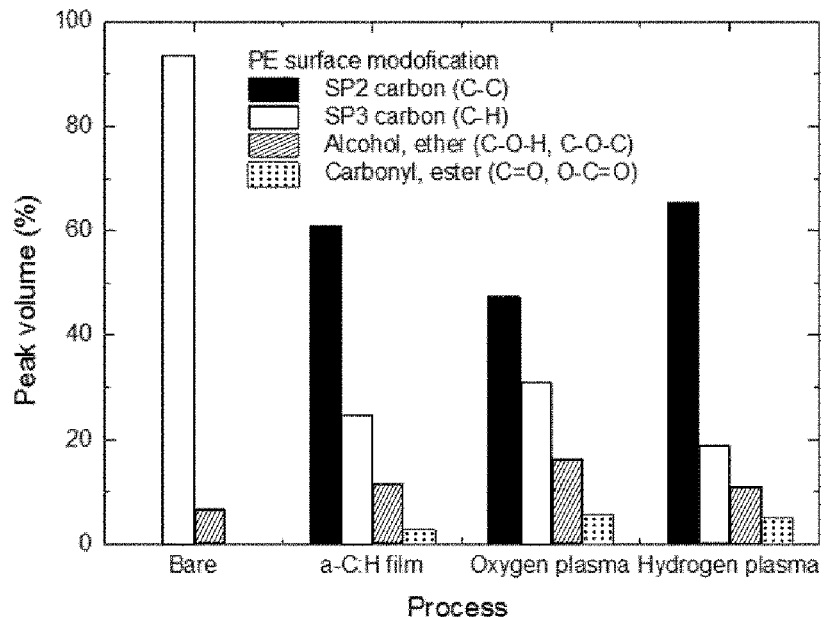
(a) PE Tube C1s peaks
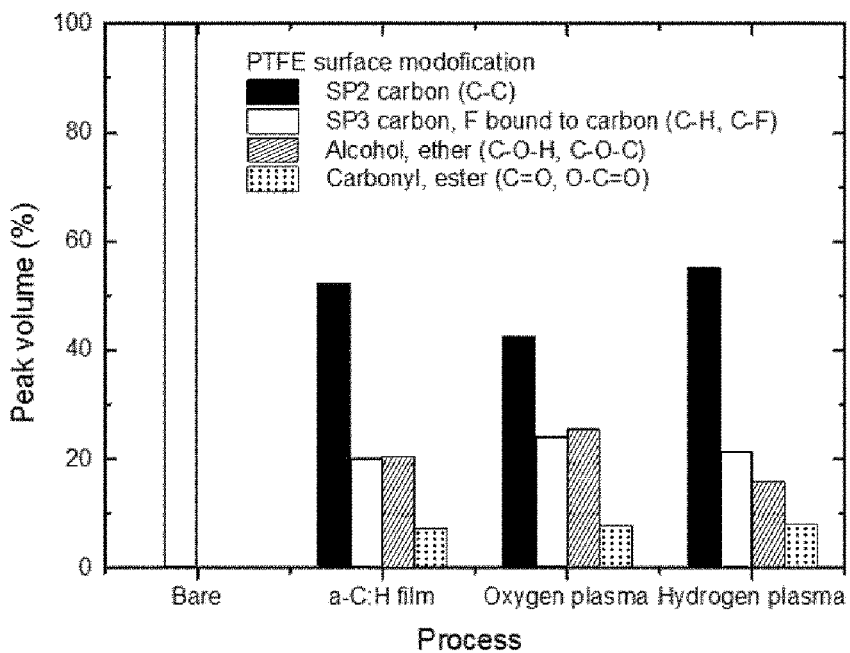
(b) PTFE Tube C1s peaks

METHOD FOR GENERATING PLASMA UNIFORMLY ON DIELECTRIC MATERIAL

CROSS-REFERENCE TO RELATED APPLICATIONS

This application claims the benefit under 35 USC 119(a) of Korean Patent Application No. 10-2014-0119310 filed on Sep. 5, 2014 in the Korean Intellectual Property Office, the entire disclosure of which is incorporated herein by reference for all purposes.

FIELD OF INVENTION

The present invention relates to a method for checking a discharge inception voltage; a method for forming a displacement field (D) inside of a dielectric material having an electric polarization density (P), comprising a step of applying a voltage the same as or higher than the discharge inception voltage obtained above by applying an external electric field to the dielectric material to which electrodes are connected; a method for forming plasma on the entire surface of a dielectric material comprising steps of injecting reaction gases and applying a voltage the same as or higher than the discharge inception voltage obtained above to the dielectric material to which electrodes are connected; a method for forming a displacement field on the entire surface of the dielectric material comprising a step of applying a voltage the same as or higher than the discharge inception voltage obtained above to the dielectric material to which electrodes are connected; and a dielectric material which is modified by treating the entire surface with plasma via the method described above.

BACKGROUND ART

A stent is a medical device placed in the body when there is abnormal circulation of blood and body fluid. The stent is typically inserted into blood vessels for the expansion of blood vessels that have been narrowed by lesions, and functions to open the blood vessels. Further, it is used to expand the digestive organs narrowed by lesions in the digestive tract and to release biological fluids into another passageway in case of blockage in the digestive tract, in addition to blood vessels. Stents made of materials including shape-memory alloys or polymers are used for the digestive tract, however, the use of those metal stents is limited as they are expensive.

The use of stents made of polymers is expected to increase due to relatively low price. However, in the case of polymer stents having a short diameter due to lack of expansibility compared to metal stents, they cannot function as a stent for a long period of time as biological materials may easily adhere to the inside thereof. Accordingly, it is important to prevent the adhesion of biological materials inside the stent when polymer stents are used. The adhesion of biological materials may lead to the formation of a bio-film due to adsorption of fibers from the digestive organs by food, proteins of biological fluid, etc., thereby narrowing the stent, which is then unable to function. Accordingly, the adhesion of biological materials must be minimized in order for the stents to function and to be used for a long time.

A method for treating vascular diseases includes a technique that uses artificial blood vessels, in addition to the stents which are prosthetic medical devices. Vascular diseases are mainly caused by thickening of arteries due to fat accumulation, or plaque (or atheroma), leading to hardening of the arteries. The arteries supply blood, oxygen, and nutrients from the heart to all parts of the body. Therefore, the arteries that have become narrow and stiff may result in restricted blood flow and a decrease in supplying these materials to each organ. Such an inadequate supply of blood may lead to dysfunction, tissue damage, and even death in severe cases. Therefore, drugs that help relax arteries are administered in order to treat such vascular diseases, however, a treatment with drugs merely improves the symptoms. There is little cure for the vascular diseases, and thus it is inconvenient that patients need to take the drugs for life. Another treatment method includes surgery in which damaged vessels are removed and artificial vessels are transplanted to the affected site.

Although methods of transplanting arteries or veins of donors have been initially implemented, they suffer from low success rates due to rejection or sclerosis. Hence, research and development into synthetic (artificial) blood vessels has been conducted. Artificial blood vessels for transplantation must be made of materials which are harmless to the human body and have high biocompatibility. Furthermore, these materials should not be rejected by the immune system and should be maintainable in vivo for a long time. Also, there should be no case in which blood vessels are clogged by precipitation of proteins or lipids or due to thrombosis.

As such, polymer materials are being used as biomaterials which can be used for stents, artificial blood vessels, etc., due to high biostability. As described above, it is important that the inside and outside of a transplant be uniformly modified to have appropriate features in order to prevent side effects by inhibiting precipitation of proteins or lipids, or thrombosis, and to improve an engraftment of the transplant by improving cell adhesion. However, polymers are typical insulators, which have low permittivity, and therefore plasma can hardly be generated, thereby imposing limitations on a surface treatment by plasma. Specifically, surface modifications with uniformity cannot be easily achieved by a common surface treatment method in the case of an inner wall of a tube having a small internal diameter, such as small-diameter stents or artificial blood vessels, or an artificial organ having an irregular shape, such as an artificial heart.

DISCLOSURE

Technical Problem

The inventors of the present invention have made extensive efforts to find a method for generating plasma from the surfaces of materials, having low permittivity, such as polymers, that is, a dielectric material, and as a result, when a predetermined voltage of an external electric field, for example, a voltage the same as or higher than the discharge inception voltage, is applied, a displacement field is formed inside of the dielectric material, which uniformly generates plasma on the entire surface of the dielectric material, confirming the possibility of a uniform surface treatment using plasma, and thereby completing the present invention.

Technical Solution

In a first aspect, the present invention provides a method for checking a discharge inception voltage of a dielectric material having a first surface and a second surface, wherein the method comprises a step of determining a voltage, at which a relationship between a measured voltage applied thereto and a measured current becomes directly proportionate, as a discharge inception voltage, by connecting electrodes to the second surface of the dielectric material, and applying the voltage under the condition that the pressure ($P_1$) applied to the first surface of the dielectric material is less than the pressure ($P_2$) applied to the second surface.

In a second aspect, the present invention provides a method for forming a displacement field on a first surface of a dielectric material having a first surface and a second surface to which electrodes are connected, wherein the method comprises a first step of applying a voltage which is the same as or higher than the discharge inception voltage obtained from the method described in the first aspect, depending on the distance between the electrodes, the pressure applied to the first surface, or the permittivity or thickness of the dielectric material, under the condition that the pressure ($P_1$) applied to the first surface of the dielectric material is less than the pressure ($P_2$) applied to the second surface.

In a third aspect, the present invention provides a method for forming plasma on an entire first surface of a dielectric material having a first surface and a second surface to which electrodes are connected, wherein the method comprises steps of injecting reaction gases into a side facing the first surface of the dielectric material; and applying a voltage which is the same as or higher than the discharge inception voltage obtained from the method described in the first aspect, depending on the distance between the electrodes, the pressure applied to the first surface, or the permittivity or thickness of the dielectric material, under the condition that the pressure ($P_1$) applied to the first surface of the dielectric material is less than the pressure ($P_2$) applied to the second surface.

In a fourth aspect, the present invention provides a method for forming a displacement field on an entire first surface of a dielectric material having a first surface and a second surface to which electrodes are connected, wherein the method comprises a step of applying a voltage which is the same as or higher than the discharge inception voltage obtained from the method described in the first aspect, depending on the distance between the electrodes, the pressure applied to the first surface, or the permittivity or thickness of the dielectric material, under the condition that the pressure ($P_1$) applied to the first surface of the dielectric material is less than the pressure ($P_2$) applied to the second surface.

In a fifth aspect, the present invention provides a dielectric material which is modified, wherein the entire first surface of the dielectric material, having a first surface and a second surface to which electrodes are connected, is treated with plasma by the method of the third aspect.

Hereinafter, the present invention will be explained in detail.

The present invention is based on the first confirmation that a displacement field can be formed on the entire surface of a dielectric material by an external electric field when a voltage the same as or higher than a certain level is applied by directly connecting the electrodes to one surface applied with a higher pressure than the other surface of the dielectric material of which two surfaces are applied with different pressures. That is, when a voltage the same as or higher than a certain level was applied, it was confirmed that plasma was formed on the surfaces of the dielectric material and the intensity of a current measured increased proportionally to the magnitude of the voltage applied thereto. Herein, the voltage where a current starts to increase in proportion to the above voltage is called a discharge inception voltage, and it was confirmed that the discharge inception voltage varies according to the distance between electrodes, the pressure applied to the surfaces of the dielectric material, the permittivity or thickness thereof, or the type and pressure of the reaction gases further injected. Accordingly, the discharge inception voltage according to these conditions can be measured, databased, and subsequently, the discharge inception voltage can be determined or predicted therefrom under specific conditions.

Moreover, since a displacement field can be formed on the entire surface of the dielectric material via the method described above, reaction gases capable of providing plasma to be generated may be injected into the surface to which a low pressure is applied, and a voltage the same as or higher than the corresponding discharge inception voltage may be applied. Therefore, plasma can be generated uniformly on the dielectric material, and subsequently, the surfaces thereof can be uniformly modified using the same.

For example, stents, artificial blood vessels, artificial organs, etc., to be inserted into the human body are not only harmless thereto and have biocompatibility, but also are not rejected by the immune system, are maintainable in the body for a long time, remain free from clogging caused by precipitation of proteins or lipids or due to thrombosis, and have an advantage of engraftment as the adhesion of blood vessel cells is facilitated. However, general biocompatible materials, for example, biocompatible polymers, cannot exert all these features, and thus modifications, such as appropriate surface treatment, may be used to help exert desirable features. Although various methods demonstrating modifications of the surfaces of conventional biocompatible materials are known in the art, it is still challenging to uniformly modify the inner wall of a tube, etc., having a diameter of several millimeter or less (e.g., 4 mm) over the entire length to have constant features. Accordingly, other inventors have designed a method for modifying the inner surface by generating microplasma from the inside of a tube, however the conventional method for generating plasma, including microplasma, from the surfaces of dielectric materials showed that the density of plasma generated was dependent on the distance from which electrodes are located. Thus, it was impossible to uniformly treat the inner wall of the tube, having a distance from as short as several centimeters to as long as several meters, with plasma. That is, plasma is locally formed only within the range of tens of micrometers to a maximum of several millimeters from the position where the electrodes are located, and even within the corresponding range, the intensity thereof rapidly decreases as the distance from the electrodes increases, and thus it is impossible to uniformly treat the surfaces of the dielectric material within the range of, for example, several centimeters using the conventional microplasma.

However, when a voltage the same as or higher than the discharge inception voltage determined according to the present invention is applied by directly connecting the electrodes to one surface applied with a higher pressure than the other surface of the dielectric material of which two surfaces are applied with different pressures, a displacement field can be formed over the entire surface of the dielectric material, and accordingly, the entire surface of the dielectric material where a lower pressure is applied can be modified with plasma by generating plasma therefrom, in which the reaction gases to be treated are injected to the opposite side of that with electrodes connected and the voltage the same as or higher than the discharge inception voltage is applied (FIG. 6).

The term "dielectric material" used herein refers to an electrical insulator capable of polarization when an external electric field is applied. Accordingly, unlike conductors, they do not transfer charges in the electric field. Preferably, the dielectric material may have a dielectric constant ($\varepsilon_r$) of 4 or less in permittivity (permittivity; $\varepsilon=\varepsilon_r\varepsilon_0$; F/m). The permittivity is a physical measure that exhibits the effect of a medium between charges on an electric field when the electric field is applied between the charges, and it may exhibit a charge amount that the medium can store.

Preferably, the dielectric material may be made of materials comprising polymers or glass. Further, the dielectric material may be a compound comprising at least two components. For example, it may be prepared with a mixture having at least two components, or may be composed of multiple layers formed by lamination of each single layer consisting of different components.

Preferably, the dielectric material may have both an inner surface and an outer surface. Further the dielectric material may be a tubular type, pouch type, or planar type, but is not limited thereto.

Preferably, the pressure difference between $P_2$ and $P_1$ may be greater than or equal to 100 Torr, and $P_1$ may be less than or equal to 10 Torr. If the pressure difference between $P_2$ and $P_1$ is greater than or equal to 100 Torr, it is possible that a plasma discharge may not occur on the $P_2$ side, but selectively occur on the $P_1$ side, which has a relatively lower pressure. This is attributed to the fact that a plasma discharge inception voltage varies depending on pressures applied, and the discharge inception voltages within the pressure range of $10^{-2}$ Torr to 10 Torr are low compared to those of outside of the pressure range (FIG. 3a). According to the features of plasma discharge, the pressure and the distance between electrodes may have an influence on the discharge inception voltage even for the dielectric materials, and when $P_2$ is less than 100 Torr, a corona discharge can occur on the surfaces of the dielectric materials as long as conditions for the discharge inception voltages are met.

A vacuum device can be used to control the pressure in the way mentioned above, and the vacuum device may be equipped with a gas supply device for injecting reaction gases, etc., and/or a vacuum exhaust device.

Preferably, the voltage applied is of an alternating current type whose frequency is in the range of 1 kHz to 100 kHz. Herein, the voltage may be applied as an alternating current having a maximum negative voltage and a maximum positive voltage of less than or equal to 20 kV of amplitude (peak to peak), but is not limited thereto.

The plasma formed by the method according to the present invention is formed uniformly on the dielectric material without any limitations on the shape or size thereof. Thus, it can be useful for modifications of the surfaces of the dielectric material.

Preferably, the degree of hydrophilicity and hydrophobicity of the entire first surface of the dielectric material may be controlled by changing reaction conditions. For example, it can be modified to have desired features, from super hydrophobicity to hydrophilicity of the surfaces of the dielectric materials, by selecting appropriate reaction gases and controlling pressure, treatment time, etc.

Further, preferably, upon using different reaction conditions, for example, changing the composition and type of reaction gases, the modification processes may be repeatedly performed to achieve desired physical properties. For example, an aging prevention layer or a layer for adhesion may be further formed on the modified surfaces of the dielectric materials by integrating hydrocarbon precursor materials using plasma. The integration of the hydrocarbon precursor materials may be achieved by plasma polymerization using a gas mixture of acetylene and argon as a reaction gas.

As such, the dielectric material with modified surfaces can be used as an in vivo transplant. The non-limiting examples of the dielectric material capable of modifying the surfaces thereof by treating plasma via the method of the present invention for the use as an in vivo transplant include super hydrophobic fluorinated hydrocarbon-based polymer tubes made of polytetrafluoroethylene (PTFE), fluorinated ethylene propylene copolymer (FEP), ethylene tetrafluoroethylene copolymer, ethylene chlorotrifluoroethylene (ETFE), perfluoroalkoxy (PEA), or polyvinylidene fluoride (PVDF); and biocompatible polymers made of polyethylene terephthalate (PET), poly(2-hydroxyethyl methacrylate) (PHEMA), polyvinylpyrrolidone (PVP), polyethylene (PE), polyethylene glycol (PEG) (also known as polyethylene oxide (PEO) or polyoxyethylene (POE)), polyvinyl alcohol (PVOH, PVA or PVAl), polypropylene (PP), or polyurethane (PU).

Advantageous Effects

The method for forming plasma of the present invention may generate plasma uniformly on the dielectric material, regardless of its shape, by applying a voltage the same as or higher than the corresponding voltage by checking the discharge inception voltage generated by a displacement field of the dielectric material. The uniformly generated plasma enables surface treatments of the inner walls of the narrow tubes such as stents or artificial blood vessels, etc., thereby allowing modifications in which the degree of hydrophilicity and hydrophobicity is controlled, and thus can be useful for surface treatments of transplants intended for purposes such as cell adhesion ability improvement for preventing deposition of proteins or lipids and/or improving the rate of engraftment.

BRIEF DESCRIPTION OF DRAWINGS

FIG. 1 shows an embodiment of a device equipped with a vacuum device for a plasma surface treatment of the present invention.

FIG. 2 schematically shows a method of electrode application for generating plasma from a dielectric material.

FIG. 3 shows graphs illustrating the relationship between a discharge inception voltage and a combination of pressure and distance between electrodes, inner diameter of a polymer tube, a type of reaction gas, or a mixing ratio of reaction gases. Breakdown voltage refers to a discharge inception voltage.

FIG. 4 shows graphs of currents relative to applied voltages measured from a plasma power supply of the present invention.

FIG. 5 schematically shows a method of electric field application for plasma using conventional high dielectric materials.

FIG. 6 shows images of plasma uniformly formed only in a tube by applying a voltage the same as or higher than the discharge inception voltage and varying the pressure inside and outside of polymer tubes.

FIG. 7 schematically shows various devices for forming plasma in a tube under a vacuum condition.

FIG. 8 schematically shows various devices for forming plasma in a tube under an atmospheric condition.

FIG. 9 schematically shows layers having various features formed on the inner surface of a tube by the reaction of individual steps using plasma formed by a preparation method according to the present invention.

FIG. 10 shows scanning electron microscope (SEM) images of the inner wall of a PTFE tube with or without hydrogen plasma treatment.

FIG. 11 shows SEM images of a hydrocarbon thin film deposited for 10 minutes.

FIG. 12 shows SEM images of hydrocarbon thin films deposited for (a) 20 minutes and (b) 30 minutes, respectively.

FIG. 13 shows a SEM image of a hydrocarbon thin film deposited for 10 minutes on a silicon wafer to measure thickness.

FIG. 14 shows SEM images depending on the oxygen plasma treatment time.

FIG. 15 shows SEM images of the surface modified with oxygen or nitrogen for the same time (10 minutes).

FIG. 16 shows FTIR-ATR spectra of the hydrogen plasma-treated surface depending on changes in the proportion of hydrogen gas in the reaction gases.

FIG. 17 shows FTIR-ATR spectra depending on the hydrogen plasma treatment time.

FIG. 18 shows FTIR-ATR spectra depending on the oxygen plasma treatment time.

FIG. 19 shows FTIR-ATR spectra depending on the nitrogen plasma treatment time.

FIG. 20 shows (a) XPS C1s spectra and (b) changes in components of the surface before and after hydrogen plasma treatment of the inner wall of a TPFE tube.

FIG. 21 shows the results of analysis of XPS C1s spectra on the inner wall of a PTFE tube (a) before and (b) after hydrogen plasma treatment.

FIG. 22 shows C1s spectra of the hydrocarbon thin film analyzed by XPS.

FIG. 23 shows the composition ratio of the hydrocarbon thin film whose surfaces were modified by the reaction gas using (a) oxygen and (b) nitrogen.

FIG. 24 shows XPS C1s spectra according to time taken for surface modifications using oxygen or nitrogen. (a) to (c) show surfaces treated for 10 seconds, 30 seconds, and 60 seconds, respectively, using oxygen, and (d) to (f) show surfaces treated for 3 minutes, 5 minutes, and 10 minutes, respectively, using nitrogen.

FIG. 25 shows changes in component of the surface modified via oxygen treatment for 30 seconds as measured by XPS at different depths.

FIG. 26 shows XPS C1s spectra of the surface modified via oxygen treatment for 30 seconds at different depths.

FIG. 27 shows water contact images on the modified surfaces prepared under a series of preparation conditions.

FIG. 28 shows changes in water contact angle depending on preparation conditions in tubes whose surfaces were modified with (a) oxygen and (b) nitrogen.

FIG. 29 shows the extent of culture of smooth muscle cells on the modified surfaces prepared depending on preparation conditions visualized via cytoplasmic staining.

FIG. 30 shows optical microscope images of the morphology of smooth muscle cells cultured on the inner wall of the surface-modified PTFE tube.

FIG. 31 shows water contact angle of a polyethylene polymer tube in which hydrophilicity is improved by plasma surface treatment.

FIG. 32 shows FTIR-ATR spectra of a surface treated-polyethylene polymer tube by exposing to argon and oxygen plasmas according to exposure time.

FIG. 33 shows albumin adhesion onto PE and PTEE tubes whose surfaces were treated with plasma. The albumin adhesion was confirmed on the surfaces deposited with nano-organic thin film and on the samples treated with hydrogen and oxygen plasmas after the deposition of the nano-organic thin film.

FIG. 34 shows the results of XPS surface analysis of samples before and after the nano-organic thin film deposition, and oxygen or hydrogen plasma treatment.

FIG. 35 shows the composition ratio of carbon binding via optimization of XPS C1s spectra of samples before and after the nano-organic thin film deposition, and oxygen or hydrogen plasma treatment.

BEST MODE

Hereinafter, the present invention will be described in more detail with reference to the following examples. However, the following examples are provided for illustrative purposes only, and the scope of the present invention should not be limited thereto in any manner.

Example 1: Determination of Discharge Inception Voltage

The method for modifying surfaces of low dielectric materials using plasma was employed to generate plasma only on the surface applied with a lower pressure ($P_1$), when two sides of the dielectric material subject to a surface treatment were applied with different pressures of $P_1$ and $P_2$, respectively, using vacuum and plasma techniques as shown in FIGS. 1 and 2.

As a particular embodiment, a plasma treatment was conducted on tubes made of the low dielectric materials such as polytetrafluoroethylene and polyethylene. Plasma was generated inside of the tubes via the method for generating plasma only on the inner surface by reducing pressure inside of the tubes while maintaining that outside under the atmospheric condition and reducing pressure by using separate vacuum exhaust devices for generating a pressure difference of more than 100 Torr inside and outside of the tubes. That is, a plasma discharge was induced on the entire inside of the tubes as the electric power the same as or higher than the discharge inception voltage was applied to the dielectric material between two electrodes by a high voltage power applied to metal electrodes installed outside of the tubes, in which the tubes subject to a surface treatment were set-up such that the pressure inside thereof was lower than that of the outside.

Example 2: Change of Discharge Inception Voltage According to Reaction Conditions For generating the plasma discharge of the low dielectric materials, a discharge inception voltage varies depending on the pressure, the distance between electrodes, the type of gases, etc. Thus, to confirm such, the discharge inception voltage was measured according to materials and inner diameter (I.D.) of the tubes and the type and composition of reaction gases, and the results thereof are shown in FIG. 3. FIG. 3 shows (a) a discharge inception voltage according to the pressure and the distances between electrodes, (b) a discharge inception voltage measured of the low dielectric materials such as polytetrafluoroethylene (PTFE) and polyethylene resin (PE) having different inner diameters, (c) a discharge inception voltage measured according to varying reaction gases in a tube of polytetrafluoroethylene, and (d)

a discharge inception voltage measured by mixing argon and oxygen, as reaction gases, with different ratios. Such experimental results were consistent with the discharge inception voltage curve of Paschen's curve.

As such, considering that the discharge inception voltages vary according to the permittivity and thickness of the low dielectric materials, the vacuum pressure applied, the type of reaction gases, and the distances between electrodes, the voltage ($V_{rms}$) applied to a plasma power supply of a fluorine-based polymer tube having a different inner diameter and a measured current ($A_{rms}$) (hereinafter, referred to as rms value) corresponding thereto are shown in FIG. 4. FIG. 4 shows results of PTFE tubes having an inner diameter of (a) 3.8 mm and (b) 1.7 mm, respectively. As shown in FIG. 4, when the tubes of the low dielectric materials were applied with a voltage with slowly increasing intensity, a current also slowly increased, but the rate of increase was non-linear and a plasma discharge was not induced inside of the tubes. However, when the voltage further increased over a certain level of voltage (hereinafter, determined as a discharge inception voltage), plasma started to form inside of the tubes. Herein, the overall amount of current rapidly increased as the discharge current increased by plasma, and plasma was formed on the entire surface of the low dielectric materials. This is called as "surface plasma". As the surface plasma was formed, a relationship between the voltage and current became linear. That is, the current increased in proportion to the magnitude of the voltage applied. Such a phenomenon is different from that using CCP and ICP as a method for generating plasma using an RF power supply from an existing vacuum device as shown in FIG. 5(a) and FIG. 5(b), and the principle behind the generation is also different from that of the atmospheric plasma described in FIG. 5(c). Further, the conventional methods for generating induced plasma share the similarity of using high dielectric materials such as glass (5 to 10) or alumina (9 to 15) having a dielectric constant of 4 or higher, and a method using RF plasma (frequency: 13.56 MHz) does not generate a voltage higher than or equal to 600 V (peak to peak voltage: 1200 V), thereby not inducing the plasma discharge from the low dielectric materials.

FIG. 6 shows uniform plasma formed inside of the tubes by applying a voltage higher than equal to the discharge inception voltage and applying the different pressures inside and outside of the polymer tubes. FIG. 6 (a) shows an example of a device in which a single tube is installed and processed, and FIG. 6 (b) shows an example of a device composed of multi-strand tubes as a bundle, which are processed simultaneously. A shown in FIG. 6, it was confirmed that plasma was uniformly formed over the entire length of the tubes regardless of whether a single-strand tube was used or multiple tubes were used simultaneously.

FIG. 7 shows various devices for forming plasma by conducting vacuum exhaust under a vacuum condition according to the conditions of the discharge inception voltage described above, and FIG. 8 schematically shows various devices for forming plasma inside of a tube installed with electrodes under an atmospheric condition. Meanwhile, the cross-section of the tube formed via the above processes is schematically shown in FIG. 9. FIG. 9 schematically shows the cross-section of the tube having layers of various features by processing repeatedly using various reaction gases.

Example 3: Surface Modification for Improving Hydrophilicity and Cell Adhesion of Inner Surface of PTFE Tube Having Small Diameter 3.1 PTFE Surface Grafting Using Plasma As for a tube whose inner surface was subject to a modification according to the Examples 1 and 2, a PTFE tube, which is a biocompatible polymer, having an inner diameter of 3.8 mm was used. Prior to modification, the tube was cut to a size of 30 cm and impurities were removed from the cut surface using a $N_2$ gun. The polymer tube was connected to a mixing chamber of a plasma system, and then the pressure inside was reduced to a low pressure state using a rotary vacuum pump. Meanwhile, a copper electrode which can enclose the outside of the polymer tube was connected and fixed at a position 10 cm away from the mixing chamber. An alternating current power supply was connected to the copper electrode, and a ground electrode was connected to a position at which the tube and the mixing chamber were connected.

As for the PTFE tube having an inner diameter of 3.8 mm, preferentially, plasma was used to modify the inner surface of the tube, and hydrogen ($H_2$, 99.99%) and argon (Ar, 99.99%) were used as reaction gases. Using a mass flow controller (MFC), hydrogen gas and argon gas were respectively fed at 50 sccm and 10 sccm into the mixing chamber, and the gas mixture was allowed to flow into the PTFE tube. An AC power supply having a frequency of 40 kHz and a maximum voltage of 2 kV was used as a plasma generator, and the inner surface of the PTFE tube was subjected to plasma treatment at 70 W for 10 minutes. During the plasma treatment, the inner pressure of the tube was maintained at 430 mTorr. Herein, the frequency was 40 kHz, and the voltage was 1.2 kV. Fluorine on the inner surface of the PTFE tube was partially substituted with hydrogen via the plasma treatment.

3.2 Introduction of Nano-Organic Thin Film Layer Using Plasma Polymerization

In order to form a nano-organic thin film after surface treatment, acetylene gas ($C_2H_2$, 99.99%) was used, and argon gas of 20 sccm was fed into the mixing chamber to induce efficient discharge. The vacuum state of the tube was maintained using a rotary pump, and the inner pressure of the tube containing acetylene gas and argon gas was kept at 300 mTorr. The thin film deposition time was from 2 minutes to 10 minutes. The deposition process performed in the microplasma resulted in forming an amorphous hydrocarbon thin film via a plasma polymerization reaction by a radical.

3.3 Surface Activation Using Reaction Gases

The surface deposited with a nano-organic thin film, that is, the amorphous hydrocarbon thin film, was modified using a reaction gas so as to have bioactivity. To this end, oxygen ($O_2$, 99.99%) gas and nitrogen ($N_2$, 99.99%) gas were separately used. In the case of surface modification using oxygen, oxygen and argon were fed at 20 sccm each into the mixing chamber using MFC. At this time, the inner pressure of the tube was maintained at 250 mTorr. In the case of surface modification using nitrogen, nitrogen and argon were fed at 20 sccm each into the mixing chamber using MFC, and the inner pressure of the tube was maintained at 260 mTorr. Surface modification using oxygen or nitrogen was carried out under conditions of a plasma power of 80 W, a frequency of 40 kHz, and a voltage of 1.3 kV. Upon oxygen treatment, because a long reaction time causes etching of the thin film, the reaction was carried out for comparatively short times of 10 seconds, 30 seconds, and 60 seconds. Because nitrogen has less severe thin film etching problems, the reaction was conducted for 3 minutes, 5 minutes, and 10 minutes.

3.4 Culture and Adhesion of Smooth Muscle Cells

Rat vascular smooth muscle cells were cultured in a culture medium containing high glucose Dulbecco's modified eagle's medium (DMEM, Wel GENE Inc.) including 4500 mg/L of glucose supplemented with 10% fetal bovine serum (FBS) in which the concentration of FBS was adjusted to 20%. This culture medium was charged with 1% penicillin/streptomycin (Wel GENE Inc.) in order to prevent contamination and deterioration. The cells were cultured in a cell incubator at 37° C. and 5% $CO_2$. The cells cultured in a state of being attached to the bottom of a culture dish were washed with 1×PBS (phosphate buffered saline; 8% NaCl, 0.2 g KCl, 1.14 g $Na_2HPO_4$, 0.2 g $KH_2PO_4$/L) at intervals of two or three days, and then treated with 1× trypsin/EDTA (Wel GENE Inc.) in an amount of 2 mL, so that the cells were stripped off of the culture dish. The separation of the cells was observed using a microscope, and the reaction was stopped by adding 10 mL of a culture medium to the 100 mm culture dish, and the resulting mixture was recovered, placed in a centrifuge, and rotated at 3000 rpm for 3 minutes, whereby only the cells were recovered. The recovered cells were aliquoted again at an appropriate cell concentration in a new culture dish so that the culture continued, or the subsequent testing was conducted using the recovered cells.

To evaluate the adhesion of vascular smooth muscle cells on the surface-modified PTFE tube according to the present invention, the PTFE tube, resulting from modification to be hydrophilic, deposition with the hydrocarbon thin film, and then surface modification with oxygen or nitrogen through the procedures described in Examples 3.1 to 3.3, was cut in half and both ends thereof were closed, and smooth muscle cells were uniformly aliquoted in the tube using a pipette. After 24 hours, the culture medium was removed, the cells which were not attached to the surface of the tube were removed via washing with 1×PBS, and cytoplasms were stained with eosin B and thus changes in color of the inner surface of the tube were observed. Also, in samples without cytoplasmic staining, the cells adsorbed to the inner wall of PTFE were directly observed using an optical microscope.

Example 4: Inhibition of Protein Adhesion onto Polyethylene Tube and Fluorine-Based Tube Having Small Diameter by Plasma Surface Treatment 4.1 Plasma Surface Treatment of Polymer Tubes Having Small Diameter As a result of the plasma surface treatment of the polyethylene tube and the fluorine-based tube having an inner diameter of 3 mm or less, a discharge inception voltage was determined at a far higher level than that of the fluorine-based tube having a diameter of 3.8 mm used in Examples 1 and 3. This represents the increase in the discharge inception voltage as the inner diameter decreases as shown in FIG. 3. As to the polymer tube having a small inner diameter, the surface modification was conducted via the method shown in Example 3.

An important method in the Examples of the present invention is the formation of a nano-organic thin film and a surface modification using reactive gases. The formation of the nano-organic thin film using acetylene, and further surface modification using hydrogen ($H_2$, 99.99%) and oxygen ($O_2$, 99.99%) gases mixed with argon injected on the surface onto which the nano-organic thin film was deposited, were used to change the surface features, thereby confirming the change of protein adhesion which occurs as the surface hydrophilization or hydrophobization takes place. A surface feature was used wherein when the nano-organic thin film, an amorphous hydrocarbon thin film, is treated with hydrogen plasma, the surface becomes more hydrophobic, and when treated with oxygen plasma, the surface becomes hydrophilic. In the case of the surface modification with hydrogen and oxygen, argon gas was fed at 20 sccm, and hydrogen or oxygen gas was fed at 20 sccm into the mixing chamber using a mass flow controller (MFC), and the pressure of the tube was maintained at 300 mTorr. In the case in which plasma was generated, the surface modification was conducted with a frequency of 40 kHz and a discharge voltage of 3 kV for 1 second to 30 seconds.

As a specific example of the inhibition of protein adhesion, albumin, a representative in vivo protein, was used to confirm the adhesion of the protein.

4.2 Albumin Adhesion Test

After dissolving albumin powder (Biosesang Inc.) in Dulbecco's phosphate buffered saline (DPBS, Wel GENE Inc.) at a concentration of 50 mg/mL, the resultant was aliquoted such that the entire inside of a PE tube whose surfaces were modified would be coated therewith, and was incubated for 24 hours at room temperature. Then, albumin solution that had stayed on the tube was removed by pipetting, and the remaining albumin that was not adhered to the surface was removed by washing with distilled water several times. The protein deposited onto the tube was stained with Coomassie blue solution for 1 hour. An excess amount of Coomassie blue solution was washed with water several times, and the degree of protein deposition onto the tube was evaluated by observing the color change inside of the tube.

Experimental Example 1: Field Emission Scanning Electron Microscope (FE-SEM)

To observe changes in morphology of the inner surface of the tube in individual processes and to measure the thickness of the deposited organic thin film, FE-SEM was used. Accordingly, changes in morphology of the inner surface of the tube depending on the process steps were observed, a silicon wafer was inserted into the tube, and the thickness of a hydrocarbon thin film formed thereon was measured, thereby determining the thickness of the thin film formed on the inner surface of the PTFE tube. The device used was JSM-7001F, the accelerating voltage was 0.2 kV to 30 kV, the resolution was 3 nm at 1 kV and was 1.2 nm at 30 kV, and magnification was in the range of ten times to 1 million times.

FIG. 10 shows SEM images of the inner wall of a PTFE tube before and after hydrogen plasma treatment. After hydrogen plasma treatment on PTFE, the surface of the PTFE tube was confirmed to be flattened while maintaining the inner structure thereof.

FIG. 11 shows SEM images of the surface having the amorphous hydrocarbon thin film deposited for 10 minutes using acetylene gas. The uniform thin film was confirmed to be deposited via plasma polymerization on the inner surface of PTFE. Also, to check whether uniformity of the thin film layer was changed depending on the thin film deposition time and to determine the optimal thin film thickness, the deposition conditions for very uniformly depositing the thin film were examined while changing the thin film deposition time. FIGS. 12(a) and 12(b) show SEM images of the amorphous hydrocarbon thin film deposited for 20 minutes and 30 minutes, respectively. Consequently, deposition for 10 minutes or longer led to a non-uniform surface and a cracked surface of the formed thin film. Thus, the optimal deposition time was set to 10 minutes. At this time, to determine the thickness of the formed hydrocarbon thin film, a silicon wafer was cut and inserted in the PTFE tube and deposition was performed under the same conditions, and the thickness of the thin film was measured using SEM. As shown in FIG. 13, the thickness of the thin film was measured to be 221.6 nm, and was confirmed to be 233.3 nm by alpha-step. From these two values, the thickness of the deposited thin film on the inner surface of the PTFE tube could be estimated, and the actual deposition thickness was subsequently measured using an XPS depth profile method.

FIG. 14 shows SEM images of the surface modified with oxygen plasma. The surface modification process using oxygen is known possibly to progress into etching. However, upon deposition for 30 seconds to 60 seconds corresponding to a comparatively short time, component coupling of the surface was changed and the effect of etching was minimized, and thereby the hydrocarbon thin film deposited in advance could be maintained.

FIG. 15 shows SEM images of the inner wall of the PTFE tube subjected to surface modification, respectively, using oxygen and nitrogen plasma for the same time (10 minutes). Consequently, the process using nitrogen was allowed to maintain the surface of the thin film deposited in advance. In the process using oxygen, however, etching occurred due to the lengthened treatment time, and thus the thin film was partially damaged, leading to a non-uniform surface. This indicates that the surface modification process using oxygen plasma must be completed within a short time of 10 minutes.

Experimental Example 2: Fourier Transform Infrared Spectroscopy (FT-IR)

To analyze the chemical binding state of the inner surface of a PTFE tube after modification in individual processes, FT-IR was used. The device used to measure the inner wall of the PTFE tube was Bruker vertex 70, and an absorption spectrum was measured from the reflected value using attenuated total reflection. The analytical range was 4000 $cm^{-1}$ to 400 $cm^{-1}$, and a beam splitter was made of KBr. The data was analyzed using OPUS program.

Specifically, the spectrum of the PTFE tube subjected to hydrogen plasma treatment was measured, and the chemical composition thereof was thus determined. While the ratio of two gases was changed in the gas mixture of argon and hydrogen used as the reaction gas, the spectra were measured and shown together. The results are shown in FIG. 16. While the plasma treatment time of 10 minutes and the amount of argon gas of 10 sccm were maintained, the amount of hydrogen gas was changed from 10 sccm to 50 sccm by intervals of 10 sccm, and thus changes in the $CH_2$ component on the surface at respective concentrations were measured. If the amount of hydrogen exceeds 50 sccm, it is impossible to generate discharge. Hence, the amount of hydrogen was maximally set to 50 sccm. As is apparent from FT-IR spectrum results of FIG. 16, peaks at 1143 $cm^{-1}$ and 1200 $cm^{-1}$ corresponded to $CF_2$ stretching of PTFE, peaks at 1575 $cm^{-1}$ and 1725 $cm^{-1}$ corresponded to C=C and C=O bonds, the peak at 2850 $cm^{-1}$ corresponded to symmetric stretching of $CH_2$, and the peak at 2920 $cm^{-1}$ corresponded to asymmetric stretching of $CH_2$. In particular, through formation of $CH_2$ bonds corresponding to peaks at 2850 $cm^{-1}$ and 2920 $cm^{-1}$ and changes in the values thereof, 50 sccm was regarded as the most effective hydrogen substitution condition.

To evaluate the effects depending on the treatment time, while the ratio of argon gas and hydrogen gas was maintained at 1:5, changes in composition over time were measured. As the plasma treatment time was increased from 5 minutes to 30 minutes at intervals of 5 minutes, FT-IR spectra were recorded. The results are shown in FIG. 17. As shown in the results, even when the plasmas treatment time was 10 minutes or longer, additional changes in composition on the surface were not observed. Ultimately, the optimal plasma treatment time required for defluorination or hydrogenation was determined to be 10 minutes. Thus, the PTFE tube subjected to plasma treatment for 10 minutes using a reaction gas comprising argon and hydrogen mixed at a ratio of 1:5 was employed in the subsequent additional surface modification testing.

Also, argon gas and acetylene gas at a ratio of 1:2 (10 sccm:20 sccm) were fed into the hydrogen plasma treated PTFE tube to perform plasma deposition, thus depositing a hydrocarbon thin film. Then the surface was further modified by plasma treatment using oxygen ($Ar:O_2$=20 sccm:20 sccm) or nitrogen (20 sccm), and changes in chemical binding of the surface modified thin film were evaluated.

FIGS. 18 and 19 show FT-IR spectra of the surface of the hydrocarbon thin film depending on the plasma treatment time using oxygen and nitrogen, respectively. Upon surface modification using oxygen plasma, peaks at 1575 $cm^{-1}$ and 1725 $cm^{-1}$, corresponding to C=C and C=O bonds, were increased, whereas peaks at 2850 $cm^{-1}$ and 2920 $cm^{-1}$, corresponding to symmetric and asymmetric binding modes of $CH_2$, were decreased. This indicates that an oxygen atom was linked to the surface of the hydrocarbon thin film, instead of preexisting hydrogen. On the other hand, upon surface modification using nitrogen plasma, as the treatment time was increased, peaks at 1575 $cm^{-1}$ and 1725 $cm^{-1}$, corresponding to C=C and C=O bonds, and peaks at 3300 $cm^{-1}$ to 3400 $cm^{-1}$, corresponding to C=N—H bonds, were increased. Furthermore, peaks at 2850 $cm^{-1}$ and 2920 $cm^{-1}$, corresponding to symmetric and asymmetric binding modes of $CH_2$, were decreased as in the treatment with oxygen plasma. This indicates that a nitrogen atom was linked to the surface of the hydrocarbon thin film, instead of preexisting hydrogen. The quantitative analysis of specific chemical components was carried out using XPS.

Experimental Example 3: X-Ray Photoelectron Spectroscopy (XPS)

Measurement of the binding state of the thin film is possible using ET-IR analysis of Experimental Example 2, but quantitative analysis is difficult using the same. Meanwhile, XPS measurement is very effective at quantitatively analyzing the chemical composition of the surface of the thin film. In the present invention, information about the composition and depth of the surface of the thin film was obtained using typical XPS and depth profile methods.

Using XPS, changes in the composition of the inner surface of the PTFE tube upon plasma treatment, formation of a nano-organic thin film, and a hydrophilic surface modification process were measured. XPS was performed using PHI 5000 Versaprobe II model with monochromatic Al—Kα (15 kV, large spot size: 800 μm, small spot size: 10 μm) as an X-ray source. To correct error generated by surface charge up, the C—H peak in the C1s spectrum was corrected to 284.5 eV. The results from the measurement were normalized based on background signals using a Shirley method, and data fitting was performed using Peakfit 4.0 (Sigmaplot) and Origin 8.1 (Origin lab) software.

The amounts of the components in individual processes as analyzed by the entire XPS scan are given in Table 1 below.

TABLE 1

| Condition | % C | % F | % O | % N |
|---|---|---|---|---|
| PTFE | 32.9 ± 0.4 | 67.1 ± 0.4 | 0 | 0 |
| H₂ treatment | 60.5 ± 0.4 | 36.8 ± 1 | 2.8 ± 0.8 | 0 |
| Hydrocarbon | 93.3 ± 2.2 | 0 | 6 ± 1.1 | 0 |
| O₂ (10 s) | 78.85 ± 0.1 | 0 | 19.9 ± 1.1 | 0.3 ± 0.4 |
| O₂ (30 s) | 78.3 ± 0.6 | 0.85 ± 1.2 | 20.4 ± 0.0 | 0 |
| O₂ (60 s) | 76.5 ± 0.6 | 1 ± 1.4 | 21.3 ± 1.3 | 0 |
| N₂ (3 min) | 73.6 ± 0.3 | 2.2 ± 0.8 | 9.995 ± 0.6 | 14.1 ± 0.4 |
| N₂ (5 min) | 74 ± 1.4 | 1.8 ± 1.6 | 11.4 ± 0.2 | 14.3 ± 1.8 |
| N₂ (10 min) | 74.1 ± 1.2 | 0.3 ± 0.6 | 10.5 ± 1.1 | 14.6 ± 1.4 |

As is apparent from Table 1, the amount of fluorine was decreased after hydrogen plasma treatment, and when the thin film was deposited, the deposited thin film caused fluorine to disappear. The formation of oxygen or nitrogen bonds on the surface of the thin film through the surface modification process using oxygen or nitrogen was confirmed.

FIG. 20 shows changes in components of the surface of PTFE before and after hydrogen plasma treatment as measured by XPS. As in FT-IR, partial defluorination of PTFE after plasma treatment occurred, and hydrogen on the surface was increased. For more detailed examination, C1s spectra were analyzed. The results are shown in FIG. 21. The total sample analysis for $CF_2$ (291.4 eV), $CH_2$ (283.5 eV), C—C, C—H (284.5 eV), C—C—H (285.5 eV) and C—O (286.6 eV), and the component analysis for CHF (290 eV) were performed. Consequently, after hydrogen plasma treatment, the carbon component coupled with fluorine was decreased and the carbon component coupled with hydrogen was formed and increased.

After introduction of the amorphous hydrocarbon thin film via plasma polymerization using acetylene gas on the tube surface-modified with hydrogen plasma treatment, XPS analysis of the surface of the hydrocarbon thin film was performed for $CH_2$ (283.5 eV), C—C, C—H (284.5 eV), and C—C—H (285.5 eV). The results are shown in FIG. 22. As seen in this drawing, fluorine is not further detected on PTFE due to the deposition of the hydrocarbon thin film, and only the hydrocarbon component was detected. The thin film was composed mostly of $CH_2$ bonds.

The surface of the hydrocarbon introduced via plasma polymerization of acetylene gas was modified using oxygen or nitrogen plasma, and then changes in the surface thereof were analyzed by XPS. The composition ratios of the resulting surface-modified hydrocarbon thin film are shown in FIG. 23. FIG. 23(a) shows the composition of the sample after oxygen plasma treatment and FIG. 23(b) shows the composition of the sample after nitrogen plasma treatment. As seen in these drawings, the proportion of C1s was decreased and oxygen or nitrogen was linked to the surface of the thin film.

To ascertain the difference in the composition depending on modification process time by the reaction gases, oxygen and nitrogen, C1s spectra were recorded. The results are shown in FIG. 24. Upon surface modification using oxygen, component analysis was performed for $CH_2$ (283.5 eV), C—C, C—H (284.5 eV), C—C—H (285.5 eV), C=O (286.8 eV) and O—C=O (288.1 eV), and upon surface modification using nitrogen, component analysis was conducted for $CH_2$ (283.5 eV), C—C, C—H (284.5 eV), C—C—H (285.5 eV), C=O (286.8 eV) and O=C—N (288.1 eV). In accordance with the progress of the surface modification of the thin film using oxygen, the C—C component was increased and the oxygen bond was formed. In particular, an increase in the C—C component indicates that the hydrocarbon thin film was partially etched by oxygen plasma.

The composition ratios of C1s spectra depending on the surface modification process time using oxygen and nitrogen are given in Tables 2 and 3 below, respectively.

TABLE 2

| | Chemical composition in at (%) | | | | |
|---|---|---|---|---|---|
| Process condition | $CH_2$ | C—C, C—H | C—C—H | C=O | O—C=O |
| Hydrocarbon | 84.2 | 7.1 | 8.7 | 0 | 0 |
| O₂ 10 s | 66.9 | 9.4 | 15.1 | 4.9 | 3.7 |
| O₂ 30 s | 63.9 | 20.1 | 9.8 | 3.7 | 2.5 |
| O₂ 60 s | 58.6 | 21.7 | 13 | 5.2 | 1.5 |

TABLE 3

| | Chemical composition in at (%) | | | | |
|---|---|---|---|---|---|
| Process condition | $CH_2$ | C—C, C—H | C—C—H | C=O | N—C=O |
| Hydrocarbon | 84.2 | 7.1 | 8.7 | 0 | 0 |
| N₂ 3 min | 75.2 | 5.8 | 10.7 | 6.7 | 1.6 |
| N₂ 5 min | 68.6 | 11.6 | 10.6 | 5 | 4.2 |
| N₂ 10 min | 64.2 | 10.4 | 17.1 | 4.8 | 3.5 |

In the case of oxygen surface modification, the surface of the thin film was confirmed to be hydrophilic via an increase in the C=O component. Also, an increase in C—C and C—H components indicates that the thin film composed of $CH_2$ was etched by oxygen plasma in a hydrocarbon matrix. The formation of a nitrogen bond was confirmed via surface modification of the thin film using nitrogen. Changes in C—C and C—H components were small because nitrogen surface modification changes only the chemical binding of the surface of the thin film and generates no etching. In the case of nitrogen surface modification, the nitrogen-carbon bond is present but the portion of a hydrophobic hydrocarbon is maintained higher, and thus hydrophilicity is considered to be lower compared to when using oxygen treatment.

To analyze the chemical composition depending on the depth of the thin film surface-modified with oxygen, an XPS depth profile method was used. The surface of the thin film was sputtered for 10 minutes (50 cycles) using an Ar ion gun (3 kV), and thus the composition distribution at different depths was analyzed. At 3 kV, sputtering of the thin film was conducted by about 30 nm each per 1 cycle. Changes in individual components depending on the sputtering time were measured. The results are shown in FIG. 25. This measurement was implemented on the sample subjected to surface modification with oxygen for 30 seconds.

As is apparent from the results of the composition ratio depending on the depth measured by XPS depth profile, the oxygen component was decreased after only 1 cycle, from which it can be ascertained that oxygen was linked to the depth of 30 nm from the surface, and that the oxygen component linked to the surface of the thin film exhibited hydrophilicity. Also, the fluorine component started being detected after about 8 minutes (40 cycles). Because the thin film is sputtered by 30 nm per 1 cycle, as mentioned above, in the case of 40 cycles, the corresponding depth approximates to 240 nm. Thereby, the thickness of the amorphous hydrocarbon thin film actually deposited on the inner surface of the PTFE tube was determined to be about 240 nm, which is similar to the thickness of the amorphous hydrocarbon thin film deposited on the silicon wafer as measured by SEM and alpha-step.

A waterfall graph for the C1s spectra of XPS depth profile is shown in FIG. 26. After 10 minutes (50 cycles) using an Ar ion gun at 3 kV, $CH_2$, which is present in the greatest amount among the components of the amorphous hydrocarbon thin film in the C1s spectra, was gradually decreased as sputtering progressed, and CHF, in which fluorine was partially substituted by hydrogen, was gradually increased. The portion where CHF was detected designates the surface of the PTFE tube substituted with hydrogen via hydrogen plasma treatment. As shown in FIG. 20, such changes indicate the presence of the hydrogen surface treatment layer occurring by replacement of fluorine atoms with hydrogen atoms in a part of the surface between the tube and the thin film.

Experimental Example 4: Measurement of Water Contact Angle (WCA)

As for changes in surface energy of the surface of the tube manufactured as above, hydrophilicity/hydrophobicity was determined by measuring a water contact angle. A tube was cut into pieces, and water contact angles on curved surfaces of the pieces of the tube were measured. Because the uneven inner surface of a piece of the tube having a small inner diameter is tested, it is difficult to accurately measure the angle, but surface energy is determined via changes in relative values. Using a sessile drop method on a piece of the tube, 3 μL of deionzied water was dropped onto the surface of a substrate, and the contact angle of the water drop was measured using a CCD camera. The obtained image and the water contact angle determined therefrom are shown in FIGS. 27 and 28, respectively.

The results of changes in water contact angle for oxygen surface modification may be associated with the composition ratio of XPS. As seen in the composition ratio of XPS, as the oxygen surface modification time increased, the proportion of oxygen was increased and the water contact angle was decreased. This means that the surface of the thin film becomes hydrophilic in the presence of more oxygen bonds. Also, in the case of nitrogen surface modification, about 10% oxygen was contained, but even when the proportion of nitrogen was higher, it did not have a great influence on hydrophilic effects. Accordingly, the water contact angle was confirmed to vary depending on the proportion of oxygen contained in the surface of the thin film.

Experimental Example 5: Optical Microscopy and Cell Staining

In order to investigate adhesion of rat vascular smooth muscle cells on tube specimens cut lengthwise, the end sides of the specimens were well enveloped to prevent out-flushing of the culture medium. A cell culture on the inner surface of the tube modified to be hydrophilic was observed using an optical microscope and observed with the naked eye via cytoplasmic staining. The cells cultured on the surface of the tube were observed using an optical microscope (GX41, magnification ×10, Olympus), thus evaluating whether smooth muscle cells were adhered to the inner surface of the tube. Also, to easily observe adhesion of the cells with the naked eye, cytoplasms were stained with eosin B (Sigma Aldrich).

The cells were aliquoted into the tube resulting from individual surface modification processes, and then cultured for 24 hours in an incubator. To observe the extent of actual adhesion of the cells with the naked eye, cytoplasms were stained with eosin B, after which changes in color of the inner wall of the PTFE tube were observed and taken by a camera. The results are shown in FIG. 29. As seen in these images, the red portion in the tube shows cell adhesion. In particular, in the tube treated with oxygen, deep red (especially, 30 seconds and 60 seconds) appeared, and the tube treated with nitrogen showed slight red (5 minutes and 10 minutes). Accordingly, in order to improve adhesion of smooth muscle cells, it was preferable that oxygen content and hydrophilicity be increased on the inner wall of the PTFE tube.

To observe whether the cells were actually adhered to the inner wall of the tube stained with red, the morphology of the adhered cells was observed using an optical microscope. The results are shown in FIG. 30, which shows optical microscope images of the tubes treated with oxygen or nitrogen having the red stained inner walls through cytoplasmic staining using eosin B. As seen in FIG. 30, a plurality of smooth muscle cells was adhered to the inner wall of the tube treated with oxygen, and the smooth muscle cells were partially attached to the tube treated with nitrogen as well. As is apparent from the microscope images, adhesion of the smooth muscle cells on the tube treated with oxygen plasma for 60 seconds was evaluated to be the greatest. This is considered to be because the tube inner surface, which is modified to be hydrophilic according to the present invention, has improved adhesion of smooth muscle cells, and thus enables adherent culture of endothelial cells of the vessel wall, making it possible to mimic artificial blood vessels. Therefore, the tube of the invention has active applications in a variety of fields.

Experimental Example 6: Plasma Surface Modifications of Polyethylene Tube

A hydrocarbon thin film, which is a nano-organic thin film, was deposited onto the inner surface of the polyethylene tube, and then, adhesion of the protein onto the surfaces of the hydrocarbon thin film, in which the surfaces thereof were further treated with plasma of hydrogen and oxygen mixed with argon, was confirmed. The surface treatment of the polyethylene tube was achieved according to Example 4, and the results of the protein adhesion experiment of the surface-treated tube were shown in FIGS. 31 to 33. FIG. 31 shows a measured water contact angle of the polyethylene tube treated with plasma which was generated by applying a voltage of 2500 V to 3000 V, and it was observed that the polyethylene tube became hydrophilic, having been hydrophobic before the surface treatment. FIG. 32 shows a graph illustrating the structural change of the surface via FT-IR analysis, which shows that the inner surface of polyethylene tubes became hydrophilic, resulting from the formation of oxygen bonds (C—O, C═O) by reactive oxygen at the surface, according to plasma exposure time.

Experimental Example 7: Albumin Adhesion Test of Surface-Modified Polymer Tube

The hydrocarbon thin film, a nano-organic thin film, was deposited onto a fluorine-based tube and a polyethylene tube using the method described in Examples 3 and 4, and the experimental results of albumin adhesion are shown in FIG. 33. Specifically, after dissolving albumin powder in Dulbecco's phosphate buffered saline at a concentration of 50 mg/mL, the resultant was aliquoted such that the entire inside of a PE tube whose surfaces were modified would be coated therewith, and was incubated for 24 hours at room temperature. Then, albumin solution that had stayed on the tube was removed by pipetting, and the remaining albumin that was not adhered to the surface was removed by washing with distilled water several times. The protein deposited onto the tube was stained with Coomassie blue solution for 1 hour. An excess amount of Coomassie blue solution was washed with water several times, and the degree of protein deposition onto the tube was evaluated by observing the color change inside of the tube.

FIGS. 33(a) and (b) show albumin adhesion onto the polyethylene tube, and it was confirmed that the amount of protein adhered to the tube decreased, that is, the albumin adhesion decreased on the surface onto which the nano-organic thin film was deposited and in the sample treated with hydrogen plasma after the deposition of the nano-organic thin film. Specifically, the albumin adhesion was hardly formed in the sample treated with hydrogen plasma even when the tube was exposed to a test solution for 7 days. However, it was confirmed that the albumin adhesion was observed in the sample treated with oxygen plasma after the deposition of the nano-organic thin film, as in the sample without surface treatment, and from this, it was also confirmed that the albumin adhesion can be controlled depending on the degree of the surface hydrophilicity and hydrophobicity. FIGS. 33(c) and (d) show the result of experimentation on the PTFE tube in the same albumin solution, and as shown in FIG. 33(c), the albumin adhesion was commonly observed in the surface treated with argon plasma, in the surface deposited with nano-organic thin film, and in the surface treated with oxygen plasma. Further, as shown in FIG. 33(d), it was confirmed that the albumin adhesion was inhibited in the sample in which hydrophobicity was increased due to hydrogen plasma treatment, as a reactive surface treatment, after the deposition of the nano-organic thin film. Consequently, the albumin adhesion significantly decreased in the sample in which hydrophobicity was increased due to hydrogen plasma treatment after the formation of the hydrocarbon thin film.

Further, the structure of the surfaces in which the albumin adhesion decreased was analyzed via an XPS surface analysis, and the results thereof are shown in FIG. 34. Specifically, the analysis was carried out after the deposition of the nano-organic thin film, followed by treatment with oxygen plasma or hydrogen plasma. FIGS. 34(a) and (b) show the results of samples of PE and PTFE polymer tubes, respectively, wherein the nano-organic thin film was deposited thereto, followed by oxygen or hydrogen plasma treatment.

First, analysis of bare PE revealed the binding energy of 283.6 eV, indicating that about 1.5 eV was shifted from 285 eV, which represents the binding state of C—C. As to an electron beam, this phenomenon appears as a charging effect, which is a feature of polymers. A partial oxygen binding state was observed as an oxygen fraction of about 2.0 at. % on the surface of PE, having a general formula of $(-CH_2-CH_2-)_n$ via the XPS component analysis. Further, the oxygen fraction increased up to about 12.9 at. % when an argon plasma treatment was carried out. However, as for the surface treatment of argon plasma, oxygen binding appears on the surface when it is exposed to the atmosphere after the treatment, and the binding of $CH_2-CH_2$ on the PE surface indicates a change.

Although there is a slight difference after the deposition of the nano-organic thin film on the surfaces of PE and PTFE, the shape of the surfaces and the binding state of carbon are substantially similar. The results for the sample in which the nano-organic thin film is deposited were fitted as in a binding state of a typical hydrocarbon thin film. In the analysis, the peaks obtained from C—C binding, C—O binding, and C═O binding were analyzed.

The binding ratios of carbon-carbon, carbon-oxygen, etc., are shown in FIG. 35 with respect to the carbon binding state after the oxygen or hydrogen treatment on the nano-organic thin film. When the deposition of the nano-organic thin film forms in both FIG. 35(a), which shows a surface analysis of PE polymer, and FIG. 35(b), which shows a surface analysis of PTFE polymer, another surface feature in common for both samples may appear that is different from existing bare materials, which indicates that the surface characteristic can be controlled according to its function regardless of polymer materials.

The oxygen plasma treatment in the plasma treatment, after the deposition of the nano-organic thin film, strongly increased the $sp^3$ C—C binding, and the composition ratio of C—O and C═O binding strongly appeared in the plasma containing oxygen. In the sample which was treated with hydrogen plasma after deposition of the hydrocarbon thin film, the fraction of $sp^3$ C—C rather decreased and that of $sp^2$ C—C slightly increased.

This indicates that the binding of hydrogen atoms to unstable carbons formed during the deposition process of hydrocarbons plays a role in decreasing the surface dangling site of the thin film and the C—O and C═O binding. This may change the —OH, —COOH, —CO— present on the functional group of —OH termination on a hydrophilic surface to the functional group of —$CH_3$, —$(C_nH_{2n+1})_m$— on —H termination, or may induce a graphitic C—C binding in which the binding with hydrogen is inhibited.

The results showing the inhibition of albumin adhesion in the sample, which underwent the deposition of hydrocarbon thin film and hydrogen plasma treatment, were observed from biological experimentation. Proteins having a very small particle size of about 3 nm are the materials that are first adhered to any surfaces by the Vroman effect. Further, proteins simultaneously having a structure of both amino acid and carboxylic acid show strong adhesion to the hydrophilic surface having a functional group of —OH termination, such as carbonyls. An electrostatic interaction and hydrogen binding are the main binding reactions of the proteins in the protein adhesion.

As for the albumin exhibiting such adhesion, the surfaces of the polymer tubes were treated with grafting of the hydrocarbon thin film and hydrogen plasma, thereby confirming that the surfaces that can inhibit the albumin adhesion can be formed. The reason therefor was that the structure of the surfaces made the surfaces unable to undergo electrostatic reactions during the surface interaction with proteins, inhibiting the protein adhesion. For this reason, the structural feature of surfaces inhibiting the albumin adhesion in the surface analysis via XPS showed that —H termination of the functional group of —$CH_3$, and —$(C_nH_{2n+1})_m$—, which is electrostatically stable, and C—C binding of graphite are formed on the surfaces to inhibit reactions with protein.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for checking a discharge inception voltage of a dielectric material having a first surface and a second surface,
    wherein the method comprises a step of determining a voltage, at which a relationship between a measured voltage applied thereto and a measured current becomes directly proportionate, as a discharge inception voltage, by connecting electrodes to the second surface of the dielectric material, and applying the voltage under the condition that the pressure ($P_1$) applied to the first surface of the dielectric material is less than the pressure ($P_2$) applied to the second surface.

2. A method for forming a displacement field on a entire first surface of a dielectric material having a first surface and a second surface to which electrodes are connected,
    wherein the method comprises a step of applying a voltage which is the same as or higher than the discharge inception voltage obtained from the method described in claim 1, depending on the distance between the electrodes, the pressure applied to the first surface, or the permittivity or thickness of the dielectric material, under the condition that the pressure ($P_1$) applied to the first surface of the dielectric material is less than the pressure ($P_2$) applied to the second surface.

3. The method of claim 2, wherein the voltage applied is of an alternating current type whose frequency is in the range of 1 kHz to 100 kHz.

4. A method for forming plasma on an entire first surface of a dielectric material having a first surface and a second surface to which electrodes are connected,
    wherein the method comprises steps of injecting reaction gases into a side facing the first surface of the dielectric material; and
    applying a voltage which is the same as or higher than the discharge inception voltage obtained from the method described in claim 1, depending on the distance between the electrodes, the pressure applied to the first surface, or the permittivity or thickness of the dielectric material, under the condition that the pressure ($P_1$) applied to the first surface of the dielectric material is less than the pressure ($P_2$) applied to the second surface.

5. The method of claim 1, wherein the voltage and current are measured upon varying the distance between the electrodes, the pressure applied to the first surface, permittivity or thickness of the dielectric material, or the type and pressure of the reaction gases further injected.

6. The method of claim 1, wherein the dielectric material has a dielectric constant of 4 or less in permittivity.

7. The method of claim 1, wherein the dielectric material is made of materials comprising polymers or glass.

8. The method of claim 1, wherein the dielectric material is a compound comprising at least two components.

9. The method of claim 1, wherein the dielectric material has both an inner surface and an outer surface.

10. The method of claim 1, wherein the dielectric material is a tubular type, pouch type, or planar type.

11. The method of claim 1, wherein the pressure difference between $P_2$ and $P_1$ is greater than or equal to 100 Torr, and $P_1$ is less than or equal to 10 Torr.

12. The method of claim 1, wherein the voltage applied is of an alternating current type whose frequency is in the range of 1 kHz to 100 kHz.

13. The method of claim 1, wherein the voltage is applied as an alternating current having a maximum negative voltage and a maximum positive voltage of less than or equal to 20 kV of amplitude.

14. The method of claim 1, wherein the pressure difference between $P_2$ and $P_1$ is greater than or equal to 100 Torr, and $P_1$ is less than or equal to 10 Torr.

15. The method of claim 1, wherein the voltage applied is of an alternating current type whose frequency is in the range of 1 kHz to 100 kHz.

16. The method of claim 1, wherein the voltage is applied as an alternating current having a maximum negative voltage and a maximum positive voltage of less than or equal to 20 kV of amplitude.

* * * * *